US006887268B2

(12) United States Patent
Butaric et al.

(10) Patent No.: US 6,887,268 B2
(45) Date of Patent: May 3, 2005

(54) EXTENSION PROSTHESIS FOR AN ARTERIAL REPAIR

(75) Inventors: Frank Butaric, Pembroke Pines, FL (US); William L. Howat, Weston, FL (US); Marc Ramer, Weston, FL (US); Kenneth S Solovay, Weston, FL (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 10/041,124

(22) Filed: Jan. 8, 2002

(65) Prior Publication Data

US 2002/0058984 A1 May 16, 2002

Related U.S. Application Data

(63) Continuation-in-part of application No. 09/714,080, filed on Nov. 16, 2000, now Pat. No. 6,656,215, and a continuation-in-part of application No. 09/714,093, filed on Nov. 16, 2000, and a continuation-in-part of application No. 09/714,079, filed on Nov. 16, 2000, now Pat. No. 6,482,227, which is a continuation-in-part of application No. 09/050,347, filed on Mar. 30, 1998, now Pat. No. 6,290,731, and a continuation-in-part of application No. 09/714,078, filed on Nov. 16, 2000, now Pat. No. 6,626,938.

(51) Int. Cl.[7] .................................................. A61F 2/06
(52) U.S. Cl. ........................ 623/1.35; 623/1.3; 623/1.16
(58) Field of Search ................................. 623/1.16, 1.3, 623/1.31, 1.35

(56) References Cited

U.S. PATENT DOCUMENTS

| 3,142,067 A | 7/1964 | Liebig |
| 3,585,707 A | 6/1971 | Stevens |
| 3,657,744 A | 4/1972 | Ersek |
| 4,140,126 A | 2/1979 | Choudhury |
| 4,169,464 A | 10/1979 | Obrez |

(Continued)

FOREIGN PATENT DOCUMENTS

| DE | D. 3205942 A1 | 9/1983 |
| EP | 0 480 667 A1 | 4/1992 |
| EP | 0 540 290 A3 | 5/1993 |
| EP | 0579523 A1 | 1/1994 |
| EP | 0 579 523 B1 | 1/1994 |
| EP | 0 615 769 A1 | 9/1994 |
| EP | 0657147 A2 | 10/1994 |
| EP | 0 666 066 A | 8/1995 |
| EP | 0686379 B1 | 12/1995 |
| EP | 9626689 A1 | 9/1996 |
| EP | 734698 A2 | 10/1996 |
| EP | 783873 A2 | 7/1997 |
| EP | 800801 A1 | 10/1997 |

(Continued)

OTHER PUBLICATIONS

Ryan et al., Bifurcated Intraluminal Prosthesis Construction and Methods, Pub. No. US 2002/0156521 A1, Pub. Date Oct. 24, 2002, application No. 09,502,942.*

Partial European Search Report EP 03250103 dated May 21, 2003.

Partial European Search Report EP 03250109 dated Jun. 13, 2003 which corresponds to related U.S. Patent 10/041,369.

EPO Search Report dated Nov. 6, 2003 for EP application 03250103.3.

EPO Search Report dated Nov. 6, 2003 for EP application 03250109.0.

EPO Search Report dated Dec. 16, 2003 for EPO Appl. No. EP 01 30 9630.

*Primary Examiner*—Bruce Snow
*Assistant Examiner*—Cheryl Miller

(57) ABSTRACT

An endoluminal aneurysm treatment system of an expandable bypass prosthesis and an extension prosthesis with a flared distal portion which, upon expansion, frictionally engages the proximal end of the bypass prosthesis.

11 Claims, 13 Drawing Sheets

U.S. PATENT DOCUMENTS

| | | |
|---|---|---|
| 4,187,390 A | 2/1980 | Gore |
| 4,317,451 A | 3/1982 | Cerwin et al. |
| 4,441,216 A | 4/1984 | Ionescu et al. |
| RE31,618 E | 7/1984 | Mano et al. |
| 4,503,569 A | 3/1985 | Dotter |
| 4,545,082 A | 10/1985 | Hood |
| 4,553,545 A | 11/1985 | Maass et al. |
| 4,562,596 A | 1/1986 | Kornberg |
| 4,570,006 A | 2/1986 | Fujii et al. |
| 4,580,568 A | 4/1986 | Glanturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes |
| 4,731,073 A | 3/1988 | Robinson |
| 4,732,152 A | 3/1988 | Wallsten |
| 4,733,665 A | 3/1988 | Palmaz |
| 4,739,762 A | 4/1988 | Palmaz |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 5,856,516 A | 8/1989 | Hillstead |
| 4,875,480 A | 10/1989 | Imbert |
| 4,886,062 A | 12/1989 | Wiktor |
| 4,907,336 A | 3/1990 | Glanturco |
| 4,913,141 A | 4/1990 | Hillstead |
| 4,925,445 A | 5/1990 | Sakamoto |
| 4,950,227 A | 8/1990 | Savin |
| 4,955,899 A | 9/1990 | Della Corna |
| 4,969,458 A | 11/1990 | Wiktor |
| 4,990,131 A | 2/1991 | Dardik |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton |
| 5,035,694 A | 7/1991 | Kasprzyk et al. |
| 5,035,706 A | 7/1991 | Gianturco et al. |
| 5,041,126 A | 8/1991 | Gianturco |
| 5,045,072 A | 9/1991 | Castillo |
| 5,064,435 A | 11/1991 | Porter |
| 5,078,726 A | 1/1992 | Kreamer |
| 5,084,065 A | 1/1992 | Weldon |
| 5,100,422 A | 3/1992 | Berguer |
| 5,102,417 A | 4/1992 | Palmaz |
| 5,104,399 A | 4/1992 | Lazarus |
| 5,104,400 A | 4/1992 | Berguer |
| 5,104,404 A | 4/1992 | Wolff |
| 5,114,423 A | 5/1992 | Kasprzyk et al. |
| 5,116,365 A | 5/1992 | Hillstead |
| 5,122,154 A | 6/1992 | Rhodes |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi |
| 5,156,620 A | 10/1992 | Pigott |
| 5,159,920 A | 11/1992 | Cordon |
| 5,163,951 A | 11/1992 | Pinchuk |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Hull |
| 5,192,307 A | 3/1993 | Wall |
| 5,195,984 A | 3/1993 | Schatz |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi |
| 5,222,971 A | 6/1993 | Willard et al. |
| 5,236,447 A | 8/1993 | Kubo |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno |
| 5,290,305 A | 3/1994 | Inoue |
| 5,292,331 A | 3/1994 | Boneau |
| 5,304,197 A | 4/1994 | Pinchuk |
| 5,304,200 A | 4/1994 | Spaulding |
| 5,306,294 A | 4/1994 | Winston |
| 5,314,444 A | 5/1994 | Gianturco |
| 5,314,472 A | 5/1994 | Fontaine |
| 5,316,023 A | 5/1994 | Palmaz |
| 5,318,535 A | 6/1994 | Miraki |
| 5,321,109 A | 6/1994 | Bosse |
| 5,330,490 A | 7/1994 | Wilk |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone |
| 5,366,473 A | 11/1994 | Winston |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,328 A | 1/1995 | Morgan |
| 5,382,261 A | 1/1995 | Palmaz |
| 5,383,927 A | 1/1995 | DeGoicoechea |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Willard et al. |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,728,131 A | 6/1995 | Frantzen et al. |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |

| Patent No. | Date | Inventor(s) |
|---|---|---|
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,453,090 A | 9/1995 | Martinez et al. |
| 5,453,235 A | 9/1995 | Calcote |
| 5,456,713 A | 10/1995 | Chuter |
| 5,466,509 A | 11/1995 | Kowligi |
| 5,468,138 A | 11/1995 | Bosse |
| 5,476,506 A | 12/1995 | Lunn |
| 5,480,423 A | 1/1996 | Ravenscroft |
| 5,484,444 A | 1/1996 | Braunschweiler |
| 5,489,295 A | 2/1996 | Piplani et al. |
| 5,496,365 A | 3/1996 | Sgro |
| 5,507,767 A | 4/1996 | Maeda et al. |
| 5,507,769 A | 4/1996 | Marin |
| 5,507,771 A | 4/1996 | Gianturco |
| 5,507,995 A | 4/1996 | Schweich, Jr. et al. |
| 5,512,229 A | 4/1996 | Bosse |
| 5,522,880 A | 6/1996 | Barone |
| 5,522,881 A | 6/1996 | Lentz |
| 5,522,882 A | 6/1996 | Gaterud |
| 5,527,354 A | 6/1996 | Fontaine et al. |
| 5,549,662 A | 8/1996 | Fordenbacher |
| 5,549,663 A | 8/1996 | Cottone, Jr. |
| 5,562,698 A | 10/1996 | Parker |
| 5,562,724 A | 10/1996 | Vorwerk |
| 5,562,726 A | 10/1996 | Chuter |
| 5,569,295 A | 10/1996 | Lam |
| 5,571,170 A | 11/1996 | Palmaz |
| 5,571,171 A | 11/1996 | Barone |
| 5,571,173 A | 11/1996 | Parodi |
| 5,578,071 A | 11/1996 | Parodi |
| 5,578,072 A | 11/1996 | Barone |
| 5,591,196 A | 1/1997 | Marin et al. |
| 5,591,197 A | 1/1997 | Orth et al. |
| 5,591,228 A | 1/1997 | Edoga |
| 5,591,229 A | 1/1997 | Parodi |
| 5,593,412 A | 1/1997 | Martinez et al. |
| 5,607,464 A | 3/1997 | Trescony |
| 5,609,624 A | 3/1997 | Kalis |
| 5,609,625 A | 3/1997 | Piplani et al. |
| 5,609,627 A | * 3/1997 | Goicoechea et al. ........ 128/898 |
| 5,617,878 A | 4/1997 | Taheri |
| 5,618,300 A | 4/1997 | Marin et al. |
| 5,628,783 A | 5/1997 | Quiachon et al. |
| 5,628,786 A | 5/1997 | Banas |
| 5,628,788 A | 5/1997 | Pinchuk |
| 5,632,763 A | 5/1997 | Glastra |
| 5,632,778 A | 5/1997 | Goldstein |
| 5,634,941 A | 6/1997 | Winston et al. |
| 5,639,278 A | * 6/1997 | Dereume et al. .............. 623/1 |
| 5,641,443 A | 6/1997 | Calcote |
| 5,643,312 A | 7/1997 | Fischell et al. |
| 5,645,559 A | 7/1997 | Hachtman |
| 5,649,952 A | 7/1997 | Lam |
| 5,653,743 A | * 8/1997 | Martin ...................... 623/1.35 |
| 5,653,745 A | 8/1997 | Trescony et al. |
| 5,653,747 A | 8/1997 | Dereume |
| 5,662,700 A | 9/1997 | Lazarus |
| 5,662,703 A | 9/1997 | Matsuno et al. |
| 5,667,523 A | 9/1997 | Bynon |
| 5,669,924 A | 9/1997 | Shaknovich |
| 5,669,936 A | 9/1997 | Lazarus |
| 5,674,241 A | 10/1997 | Bley |
| 5,674,276 A | 10/1997 | Andersen et al. |
| 5,676,696 A | 10/1997 | Marcade |
| 5,676,697 A | 10/1997 | McDonald |
| 5,681,345 A | 10/1997 | Euteneuer |
| 5,681,346 A | 10/1997 | Orth et al. |
| 5,683,448 A | 11/1997 | Cragg |
| 5,683,449 A | * 11/1997 | Marcade ..................... 128/898 |
| 5,683,450 A | 11/1997 | Goicoechea et al. |
| 5,683,451 A | 11/1997 | Lenker et al. |
| 5,685,847 A | 11/1997 | Barry |
| 5,693,083 A | 12/1997 | Baker et al. |
| 5,693,084 A | 12/1997 | Chuter |
| 5,693,085 A | 12/1997 | Buirge et al. |
| 5,693,086 A | 12/1997 | Goicoechea et al. |
| 5,695,517 A | 12/1997 | Marin et al. |
| 5,697,948 A | 12/1997 | Marin et al. |
| 5,697,971 A | 12/1997 | Fischell et al. |
| 5,700,285 A | 12/1997 | Myers |
| 5,702,418 A | 12/1997 | Ravenscroft |
| 5,713,917 A | 2/1998 | Leonhardt et al. |
| 5,716,365 A | 2/1998 | Goicoechea et al. |
| 5,716,395 A | 2/1998 | Myers et al. |
| 5,718,159 A | 2/1998 | Thompson |
| 5,718,724 A | 2/1998 | Goicoechea et al. |
| 5,720,735 A | 2/1998 | Dorros |
| 5,720,776 A | 2/1998 | Chuter et al. |
| 5,723,003 A | 3/1998 | Winston |
| 5,723,004 A | 3/1998 | Dereume et al. |
| 5,725,534 A | 3/1998 | Rasmussen |
| 5,725,568 A | 3/1998 | Hastings |
| 5,725,570 A | 3/1998 | Heath |
| 5,728,065 A | 3/1998 | Follmer et al. |
| 5,728,068 A | 3/1998 | Leone et al. |
| 5,728,313 A | 3/1998 | Ritter et al. |
| 5,733,328 A | 3/1998 | Fordenbacher |
| 5,735,892 A | 4/1998 | Myers |
| 5,746,709 A | 5/1998 | Rom et al. |
| 5,749,880 A | 5/1998 | Banas et al. |
| 5,749,920 A | 5/1998 | Quiachon et al. |
| 5,749,921 A | 5/1998 | Lenker et al. |
| 5,752,966 A | 5/1998 | Chang |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,772 A | 5/1998 | Evans et al. |
| 5,755,773 A | 5/1998 | Evans et al. |
| 5,755,777 A | 5/1998 | Chuter |
| 5,758,562 A | 6/1998 | Thompson |
| 5,760,006 A | 6/1998 | Shank |
| 5,766,201 A | 6/1998 | Ravenscroft et al. |
| 5,769,882 A | 6/1998 | Fogarty et al. |
| 5,769,885 A | 6/1998 | Quiachon et al. |
| 5,776,180 A | 7/1998 | Goicoechea et al. |
| 5,782,765 A | 7/1998 | Jonkman |
| 5,782,906 A | 7/1998 | Marshall et al. |
| 5,782,909 A | 7/1998 | Quiachon et al. |
| 5,788,626 A | 8/1998 | Thompson |
| 5,797,953 A | 8/1998 | Tekulve |
| 5,800,456 A | 9/1998 | Maeda et al. |
| 5,800,508 A | 9/1998 | Goicoechea et al. |
| 5,800,516 A | 9/1998 | Fine et al. |
| 5,800,518 A | 9/1998 | Piplani et al. |
| 5,800,520 A | 9/1998 | Fogarty et al. |
| 5,810,870 A | 9/1998 | Myers |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,043 A | 10/1998 | Cottone, Jr. |
| 5,824,044 A | 10/1998 | Quiachon et al. |
| 5,824,046 A | 10/1998 | Smith |
| 5,824,054 A | 10/1998 | Khosravi |

| Patent Number | Date | Inventor |
|---|---|---|
| 5,824,055 A | 10/1998 | Spiridigliozzi et al. |
| 5,827,310 A | 10/1998 | Marin et al. |
| 5,827,320 A | 10/1998 | Richter et al. |
| 5,827,327 A | 10/1998 | McHaney |
| 5,830,229 A | 11/1998 | Konya et al. |
| 5,833,651 A | 11/1998 | Donovan et al. |
| 5,840,011 A | 11/1998 | Landgrebe et al. |
| 5,843,031 A | 12/1998 | Hermann et al. |
| 5,843,120 A | 12/1998 | Israel |
| 5,843,158 A | 12/1998 | Lenker et al. |
| 5,843,160 A | 12/1998 | Rhodes |
| 5,855,598 A | 1/1999 | Pinchuk |
| 5,857,998 A | 1/1999 | Barry |
| 5,858,556 A | 1/1999 | Eckert |
| 5,860,998 A | 1/1999 | Robinson et al. |
| 5,861,027 A | 1/1999 | Trapp |
| 5,868,777 A | 2/1999 | Lam |
| 5,871,537 A | 2/1999 | Holman et al. |
| 5,871,538 A | 2/1999 | Dereume |
| 5,876,397 A | 3/1999 | Edelman et al. |
| 5,876,449 A | 3/1999 | Starck et al. |
| 5,893,868 A | 4/1999 | Hanson et al. |
| 5,893,887 A | 4/1999 | Jayaraman |
| 5,899,890 A | 5/1999 | Chiang et al. |
| 5,902,308 A | 5/1999 | Murphy |
| 5,904,713 A | 5/1999 | Leschinsky |
| 5,906,619 A | 5/1999 | Olson et al. |
| 5,906,640 A | 5/1999 | Penn et al. |
| 5,906,641 A | 5/1999 | Thompson et al. |
| 5,908,448 A | 6/1999 | Roberts et al. |
| 5,916,263 A | 6/1999 | Goicoechea et al. |
| 5,916,264 A | 6/1999 | Von Oepen |
| 5,919,224 A | 7/1999 | Thompson et al. |
| 5,928,260 A | 7/1999 | Chin et al. |
| 5,935,667 A | 8/1999 | Calcote |
| 5,938,696 A | 8/1999 | Goicoechea et al. |
| 5,944,726 A | 8/1999 | Blaeser et al. |
| 5,944,750 A | 8/1999 | Tanner et al. |
| 5,951,599 A | 9/1999 | McCrory |
| 5,954,693 A | 9/1999 | Barry |
| 5,957,973 A | 9/1999 | Quiachon et al. |
| 5,957,974 A | 9/1999 | Thompson et al. |
| 5,961,548 A | 10/1999 | Shmulewitz |
| 5,968,069 A | 10/1999 | Dusbabek et al. |
| 5,968,088 A | 10/1999 | Hansen et al. |
| 5,980,565 A | 11/1999 | Jayaraman |
| 5,993,481 A | 11/1999 | Marcade et al. |
| 6,007,543 A | 12/1999 | Ellis et al. |
| 6,015,431 A | 1/2000 | Thornton et al. |
| 6,015,432 A | 1/2000 | Rakos et al. |
| 6,016,810 A | 1/2000 | Ravenscroft |
| 6,016,848 A | 1/2000 | Egres, Jr. |
| 6,017,363 A | 1/2000 | Hojeibane |
| 6,017,364 A | 1/2000 | Lazarus |
| 6,019,786 A | 2/2000 | Thompson |
| 6,024,763 A | 2/2000 | Lenker et al. |
| 6,027,526 A | 2/2000 | Limon et al. |
| 6,027,529 A | 2/2000 | Roychowdhury et al. |
| 6,030,413 A | 2/2000 | Lazarus |
| 6,030,415 A | 2/2000 | Chuter |
| 6,033,435 A | 3/2000 | Penn et al. |
| 6,036,697 A | 3/2000 | DiCaprio |
| 6,036,725 A | 3/2000 | Avellanet |
| 6,039,749 A | 3/2000 | Marin et al. |
| 6,039,758 A | 3/2000 | Quiachon et al. |
| 6,048,356 A | 4/2000 | Ravenscroft et al. |
| 6,051,020 A | 4/2000 | Goicoechea et al. |
| 6,056,775 A | 5/2000 | Borghi et al. |
| 6,059,821 A | 5/2000 | Anidjar et al. |
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,071,307 A | 6/2000 | Rhee et al. |
| 6,077,273 A | 6/2000 | Euteneuer et al. |
| 6,078,832 A | 6/2000 | Lenker et al. |
| 6,086,577 A | 7/2000 | Ken et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,093,199 A | 7/2000 | Brown et al. |
| 6,097,978 A | 8/2000 | Demarais et al. |
| 6,099,558 A | 8/2000 | White et al. |
| 6,099,560 A | 8/2000 | Penn et al. |
| 6,102,938 A | 8/2000 | Evans et al. |
| 6,102,940 A | 8/2000 | Robichon et al. |
| 6,102,942 A | 8/2000 | Ahari |
| 6,110,191 A | 8/2000 | Dehdashtian et al. |
| 6,110,198 A | 8/2000 | Fogarty et al. |
| 6,117,117 A | 9/2000 | Mauch |
| 6,117,156 A | 9/2000 | Richter et al. |
| 6,117,157 A | 9/2000 | Tekulve |
| 6,117,166 A | 9/2000 | Winston et al. |
| 6,117,167 A | 9/2000 | Goicoechea et al. |
| 6,123,722 A | 9/2000 | Fogarty et al. |
| 6,126,685 A | 10/2000 | Lenker et al. |
| 6,129,754 A | 10/2000 | Kanesaka et al. |
| 6,129,756 A | 10/2000 | Kugler et al. |
| 6,132,450 A | 10/2000 | Hanson et al. |
| 6,132,459 A | 10/2000 | Piplani et al. |
| 6,162,246 A * | 12/2000 | Barone ...................... 623/1.35 |
| 6,183,509 B1 | 2/2001 | Dibie |
| 6,203,568 B1 * | 3/2001 | Lombardi et al. ......... 623/1.13 |
| 6,210,429 B1 | 4/2001 | Vardi et al. |
| 6,214,040 B1 | 4/2001 | Jayaraman |
| 6,224,609 B1 | 5/2001 | Ressemann et al. |
| 6,245,099 B1 | 6/2001 | Edwin et al. |
| 6,270,525 B1 | 8/2001 | Letendre et al. |
| 6,287,335 B1 | 9/2001 | Drasler et al. |
| 6,293,965 B1 | 9/2001 | Berg et al. |
| 6,296,863 B1 | 10/2001 | Trogolo et al. |
| 6,299,634 B1 * | 10/2001 | Bergeron .................... 623/1.1 |
| 6,302,906 B1 | 10/2001 | Goicoechea et al. |
| 6,306,164 B1 | 10/2001 | Kujawski |
| 6,325,819 B1 | 12/2001 | Pavenik et al. |
| 6,325,820 B1 * | 12/2001 | Khosravi et al. .......... 623/1.13 |
| 6,325,823 B1 | 12/2001 | Horzewski et al. |
| 6,325,826 B1 | 12/2001 | Vardi et al. |
| 6,331,188 B1 | 12/2001 | Lau et al. |
| 6,334,868 B1 | 1/2002 | Ham |
| 6,344,056 B1 * | 2/2002 | Dehdashtian .............. 623/1.35 |
| 6,352,554 B2 | 3/2002 | De Paulis |
| 6,361,557 B1 | 3/2002 | Gittings et al. |
| 6,409,756 B1 * | 6/2002 | Murphy ..................... 623/1.35 |
| 6,468,301 B1 | 10/2002 | Amplatz et al. |
| 6,524,336 B1 * | 2/2003 | Papazolgou et al. ....... 623/1.35 |
| 6,576,009 B2 | 6/2003 | Ryan et al. |
| 6,596,023 B1 * | 7/2003 | Nunez et al. ................ 623/1.3 |
| 6,648,913 B1 * | 11/2003 | Yee et al. ................... 623/1.35 |
| 2001/0014823 A1 | 8/2001 | Petrick |
| 2002/0052648 A1 | 5/2002 | McGuckin, Jr. et al. |
| 2002/0193873 A1 | 12/2002 | Brucker et al. |
| 2003/0097169 A1 | 5/2003 | Brucker et al. |

FOREIGN PATENT DOCUMENTS

| | | |
|---|---|---|
| EP | 830853 A1 | 3/1998 |
| EP | 832616 A1 | 4/1998 |
| EP | 0855170 A2 | 7/1998 |
| EP | 880948 A1 | 12/1998 |
| EP | 0 904 745 A2 | 3/1999 |

| | | | | | | |
|---|---|---|---|---|---|---|
| EP | 0928606 A1 | 7/1999 | | JP | 7 24072 A | 1/1995 |
| EP | 937442 A2 | 8/1999 | | JP | 7100210 A | 4/1995 |
| EP | 0947179 A2 | 10/1999 | | JP | 6 86827 A | 6/1998 |
| EP | 1000590 A1 | 5/2000 | | RU | 1680055 | 5/1988 |
| EP | 1 086 665 A | 3/2001 | | WO | 8704935 A1 | 8/1987 |
| EP | 1 208 817 A | 5/2002 | | WO | 9516406 A1 | 6/1995 |
| EP | 1 212 989 A2 | 6/2002 | | WO | 9521592 A1 | 8/1995 |
| EP | 1 212 990 A | 6/2002 | | WO | 96/34580 A1 | 11/1996 |
| FR | 0 566 807 A1 | 2/1924 | | WO | 9724081 A1 | 7/1997 |
| FR | 2733682 A1 | 11/1996 | | WO | 9725000 A1 | 7/1997 |
| FR | 2740346 A1 | 4/1997 | | WO | 9733532 A2 | 9/1997 |
| FR | 2743293 A1 | 7/1997 | | WO | WO 97 33532 A | 9/1997 |
| FR | 2 777 460 A | 10/1999 | | WO | 9807389 A1 | 2/1998 |
| GB | 0 662 307 A2 | 9/1948 | | WO | WO 98/19628 A1 | 5/1998 |
| GB | 1 205 743 | 9/1970 | | WO | 98/19628 A1 | 5/1998 |
| JP | 5524095 A | 2/1980 | | WO | 9823322 A1 | 6/1998 |
| JP | 60220030 A | 11/1985 | | WO | 9836709 A1 | 8/1998 |
| JP | 62231657 A | 3/1988 | | WO | 9853761 A1 | 12/1998 |
| JP | 464367 A | 2/1992 | | WO | 9908744 A1 | 2/1999 |
| JP | 4263852 A | 4/1992 | | WO | 9911199 A1 | 3/1999 |
| JP | 5 76603 A | 3/1993 | | WO | WO 01 74270 A | 10/2001 |
| JP | 5 269199 A | 10/1993 | | WO | WO 02/26165 A1 | 4/2002 |
| JP | 7529 A | 10/1994 | | | | |
| JP | 6282730 A | 10/1994 | | * cited by examiner | | |

EXTENSION PROSTHESIS FOR AN ARTERIAL REPAIR

CROSS-REFERENCE TO RELATED APPLICATIONS

This application is continuation in part of U.S. application Ser. No. 09/714,080, filed on Nov. 16, 2000; U.S. application Ser. No. 09/714,093, filed on Nov. 16, 2000; U.S. application Ser. No. 09/714,079, filed on Nov. 16, 2000, now U.S. Pat. No. 6,482,227 B1 which is a Continuation-in-Part of application Ser. No. 09/050,347, filed Mar. 30, 1998, now U.S. Pat. No. 6,290,731 B1 which issued Sep. 18, 2001, and U.S. application Ser. No. 09/714,078, filed on Nov. 16, 2000.

BACKGROUND OF THE INVENTION

1. Field of the Invention

The present invention relates to devices and methods for repairing aneurysms, and more particularly, to percutaneously and/or intraluminally delivered devices and methods for repairing aneurysms, such as abdominal aortic aneurysms and thoracic aortic aneurysms.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e. catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. Their delivery procedure typically involves advanced angiographic techniques performed through vascular accesses gained via surgical cutdown of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendible and re-configurable while maintaining acute and long term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

SUMMARY OF THE INVENTION

The extension prosthesis of the present invention provides a means for anchoring and/or sealing an extension prosthesis in another by-pass prosthesis as briefly described above.

The present invention is directed to a system including at least one prosthesis for repair or replacement of a mammalian body part or condition. The typical system includes a first prosthesis for sealing the system within a predetermined portion of an artery; at least one second prosthesis engaged to the first prosthesis, said second prosthesis providing a fluid flow path through the system or a portion of the system; and a third or extension prosthesis for extending a fluid flow path through the system or a portion of the system. In some embodiments of the invention, the second prosthesis is sealingly and/or matingly engaged with the first prosthesis. In some embodiments of the invention, the extension prosthesis extends the fluid flow path formed by the second prosthesis. In some embodiments of the invention, the extension prosthesis is sealingly and/or matingly engaged with the second prosthesis.

A typical first prosthesis includes a support or stent structure, and a foam or gasket material supported by the stent, the stent and gasket material being configured to seal the system within an artery. A typical first prosthesis also includes one or more structures or elements for engaging the second prosthesis. In preferred embodiments of the invention, these elements or structures sealingly and/or matingly engage the second prosthesis. The stent is typically a synthetic or natural matrix for supporting the gasket material. In some exemplary embodiments of the stent, the stent is a hollow, substantially cylindrical, and preferably radially expandable matrix having a lumen and two open ends. The typical gasket material is a synthetic or natural fabric, tissue, foam, or the like. In preferred embodiments of the invention, the gasket material covers at least a portion of the lumen, even more preferably, the proximal end of the lumen.

A typical second and third prosthesis includes a support or stent structure, and graft material supported by the stent, the stent and graft material defining a fluid flow path therethrough. The typical graft material is a synthetic or natural fabric, tissue, or the like. The stent is typically a synthetic or natural matrix for supporting the graft and/or positioning the prosthesis in a predetermined position. In some exemplary embodiments of the stent, the stent is a hollow, substantially cylindrical, and preferably radially expandable matrix having a lumen and two open ends. The stent typically comprises a plurality of interconnected struts. In some exemplary embodiments of the invention, a graft material may be positioned on an inside and/or outside surface of the matrix; in preferred embodiments of the invention, the graft material may include a plurality of substantially longitudinally directed pleats disposed thereon. In a particularly preferred embodiment, the graft further includes a plurality of radially oriented pleat interruptions. In some exemplary embodiments of the invention the graft material may be attached to the stent, preferably by one or more staples or the like.

In some exemplary embodiments of the invention, one prosthesis may be connected to another using a suture or rivet having a knob or sphere on at least one of its ends. For example, a suture or rivet may include one or more legs having a tip configured into a knot, ball, knob, sphere or the like. It is intended that such knob element should assume a lower profile than a conventional suture knot. It is believed that a lower profile connector assembly facilitates delivery of the prosthesis to its intended site.

A system according to the present invention is intended for repairing or bypassing an aneurysm, preferably an aortic aneurysm. The system may also be used to direct fluid flow from one portion of a fluid pathway to another.

The system, apparatus, and method of the present invention provides a third prosthesis or extension prosthesis. In practice, the internal diameter of an artery effects the length of a second prosthesis that can be delivered to the sight of the aneurysm due to the device-foreshortening phenomenon. One skilled in the art will readily recognize that this effective length is different for each patient. In accordance with the present invention, the third or extension prosthesis may be used or incorporated into the system when the length of the second prosthesis is insufficient to bridge the portion of the artery between the position of the first prosthesis and an artery or arteries downstream of the aneurysm.

The accompanying figures show illustrative embodiments of the invention from which these and other of the objectives, novel features and advantages will be readily apparent.

BRIEF DESCRIPTION OF THE DRAWINGS

The foregoing and other aspects of the present invention will best be appreciated with reference to the detailed description of the invention in conjunction with the accompanying drawings. Throughout the figures and the description below, like numerals indicate the same element.

DETAILED DESCRIPTION OF THE PREFERRED EMBODIMENTS

Figure 1:
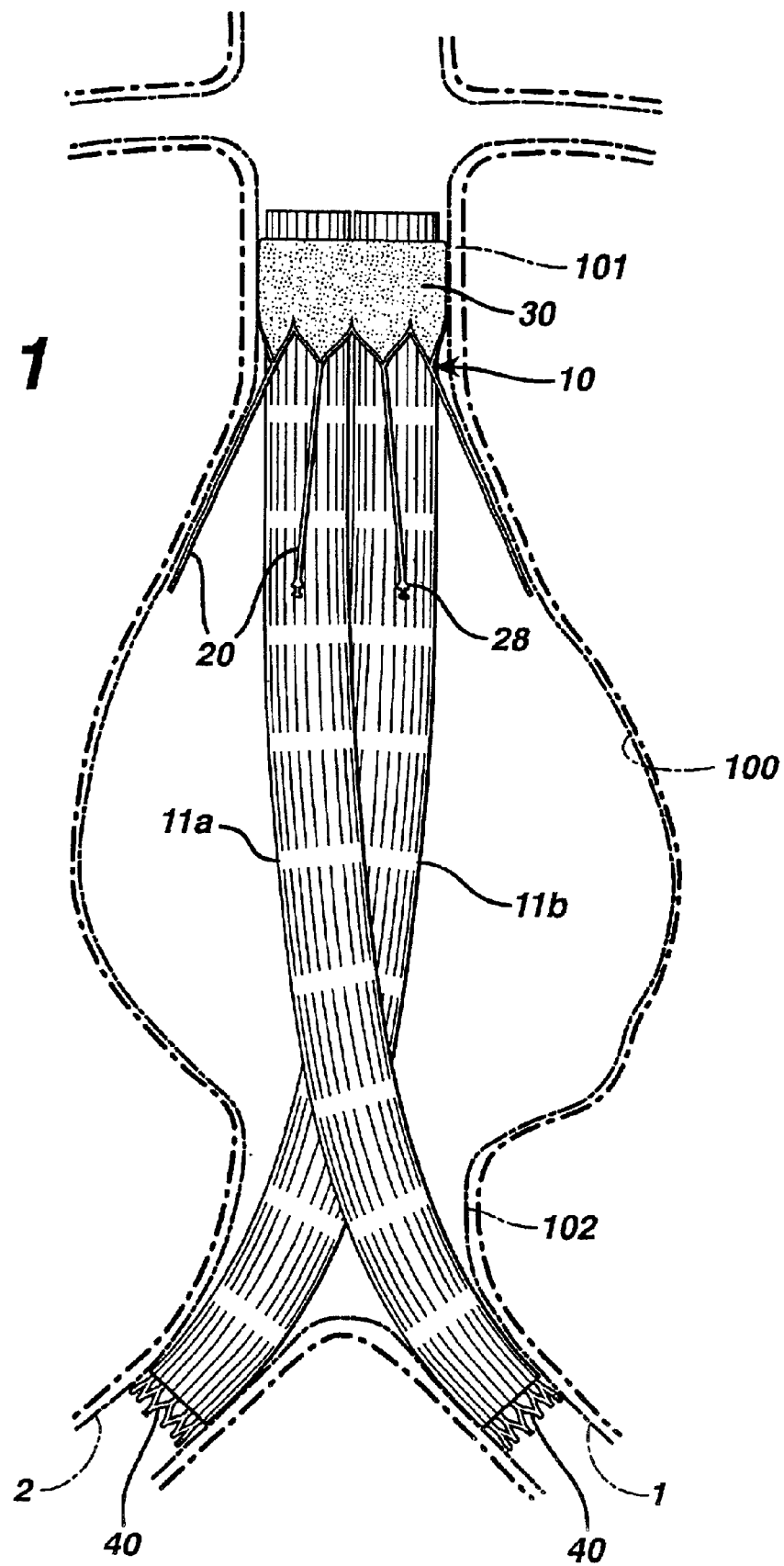
FIG. 1 is an elevation view of a fully deployed aortic repair system made in accordance with the present invention.

The apparatuses, systems, methods, and kits of the present invention may be used in the treatment of aortic aneurysms, preferably an abdominal aortic aneurysm, among other uses noted below. A better understanding of the present device and its use in treating abdominal aortic aneurysms will be achieved by reading the following description in conjunction with the above-incorporated references.

The present invention is directed to a system for treating or repairing an aneurysm, the system comprising a first prosthesis, a second prosthesis adapted to engage a portion of the first prosthesis, and a third or extension prosthesis adapted to engage the second prosthesis. In some embodiments of the invention, the second prosthesis engages a proximal portion of the first prosthesis. In some embodiments of the invention, the third prosthesis engages the second prosthesis and extends distally or downstream of the system; in some embodiments of the invention, the third prosthesis engages the second prosthesis and extends proximally or upstream of the system. In some embodiments of the invention, the system may include an extension prosthesis that extends distally and an extension prosthesis that extends proximally.

A system according to the present invention includes a bypass prosthesis and at least one extension prosthesis, the extension prosthesis being configured to matingly engage a portion of the bypass prosthesis. In preferred embodiments of the invention, the system also includes a first prosthesis configured to receive a portion of the bypass prosthesis.

The present invention is also directed to a system for repairing an aneurysm, said system being variously configured and/or assembled using components described in more detail below. Typical systems according to this aspect of the invention may include one or more first prostheses or a sealing component, one or more second prostheses or a fluid flow component, and, optionally, one or more component receptacles, assemblies, or connectors for matingly engaging one component with another. Preferred embodiments of a system of the present invention include a sealing component matingly engaged to two fluid flow path components.

In preferred embodiments of the invention, the second prosthesis includes at least one first marker and the third prosthesis includes at least one second marker, the first marker and the second marker being positioned relative to the other to align the second prosthesis with the third prosthesis under fluoroscopy in vivo.

The present invention is directed to an extension prosthesis intended to matingly engage and extend or lengthen an existing prosthesis. In preferred embodiments of the invention, the extension prosthesis extends or lengthens a fluid flow path formed or defined by a second prosthesis. The extension prosthesis of the present invention preferably includes a stent having an inner and an outer surface, and having a graft material disposed on the inner surface, the outer surface, or combinations thereof. In preferred embodiments of the invention, the extension prosthesis also includes one or more markers for positioning the extension prosthesis in vivo in relation to another prosthesis in the system. The extension prosthesis may also include one or more connectors for matingly engaging another prosthesis, and/or in relation to its position in vivo.

The present invention also includes an extension prosthesis stapled to a first prosthesis in vivo.

The present invention also includes an extension prosthesis comprising a graft material supported by a stent, wherein the graft material is matingly engaged to the stent using one or more staple rivets. As used herein, a staple rivet refers to a conventional staple having its ends formed into a ball after the staple rivet passes through the stent and graft material.

The present invention also includes a method for extending one or more fluid flow paths. The method includes providing an extension prosthesis according to the invention, and matingly engaging the extension prosthesis with the second prosthesis in vivo. The method may also include delivering the extension prosthesis to the site of the aneurysm and/or to the site of one or more other prostheses. In preferred embodiments of the invention, the method includes connecting a second prosthesis with an extension prosthesis, and establishing a fluid flow path therebetween.

The present invention also includes a method for repairing an aneurysm when a second prosthesis is too short to fully by-pass the aneurysm. The method includes providing an extension or third prosthesis according to the invention, and matingly engaging the extension prosthesis with the second prosthesis in vivo. The method may also include delivering the extension prosthesis to the site of the aneurysm and/or a prosthesis of the system. In preferred embodiments of the invention, the method includes connecting a second prosthesis with an extension prosthesis, and establishing a fluid flow path therebetween.

The present invention is also directed to a kit comprising one or more prostheses according to the invention, preferably in a sterile or sterilizable enclosure.

A system or kit of the present invention may include one or more modular components. As used herein, a modular component is configured, or adapted to engage, or includes one or more structures that are intended to communicate with or engage a complementary structure on another modular component. The present invention also includes a kit that includes one or more of the following: a sterile or sterilizable enclosure; a first prosthesis; a first prosthesis in an individual sterile enclosure; a second prosthesis; a second prosthesis in an individual sterile enclosure; a third prosthesis; a third prosthesis in an individual sterile enclosure; at least one suture; at least one staple; a collar or catheter tip assembly configured to engage and deliver a first prosthesis, a second prosthesis, and/or a third prosthesis; and at least one marker configured for placement on a first prosthesis, a second prosthesis, a third prosthesis, and/or portions thereof.

Embodiments of the invention may further include one or more bypass prostheses configured to matingly engage a first prosthesis, the bypass prosthesis comprising a graft material engaging a stent, the stent comprising a hollow matrix comprising a series of interconnected struts, the matrix being moveable from a first closed position to a second open position; the stent having at least one attachment structure or connector for matingly engaging at least one second complementary structure on the first prosthesis. In some exemplary embodiments of the invention, the prosthesis further comprises at least one marker. In preferred embodiments of the invention, the marker or markers are positioned on or formed as part of the stent.

Definitions

As used herein, aortic aneurysm refers to any failure of a conduit, such as an aortic wall, typically characterized by an undesirable dilation of a portion of the artery, vessel malformation, or an occlusion. An exemplary use of a system and method of the present invention is to repair an aortic aneurysm, and the use of such term is not intended to limit the use of the structures or systems of the present invention to repair or replace other conduit failures. The system and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. In preferred embodiments of the invention, the system and structures are used to treat, repair, replace, or bypass an abdominal aortic aneurysm.

As used herein fluid pathway refers to any in vivo structure through which a biological fluid passes. A preferred fluid pathway is an artery. Fluid pathways include, but are not limited to channels formed by an artery, a vein, a capillary, lymph nodes and channels, and arteries, veins, and capillaries within an organ or organelle.

As used herein fluid or biological fluid refers to any fluid produced by an animal, including a human. Exemplary biological fluids include but are not limited to blood, oxygenated blood, de-oxygenated blood, gastric fluids, amniotic fluid, cerebro spinal fluid, and lymph. The preferred fluid is blood or oxygenated blood.

As used herein, conduit typically refers to any structure used to convey a biological fluid. The conduit may be formed of natural or synthetic materials or combinations thereof. Exemplary conduits include but are not limited to an artery, a vein, a capillary, lymph nodes and channels, and arteries, veins, and capillaries within an organ or organelle.

As used herein, "biofusion" is a word coined by assignee referring to the ability of cells, proteins, fibrin, and other biological molecules to incorporate into the pore structure of a material, such as a foam or gasket material, or a graft material. It is believed that this feature promotes a long term stable biological interface that cannot be separated about six weeks after implantation.

The biofusion effect has many advantages. It has the potential to obviate late endo-leakage by preventing areas of non-organized clots from being displaced or recanalized. It is also believed that biofusion creates a connective tissue collar around the prosthesis that may prevent the aortic neck from dilating over time. Restricting neck dilation avoids leakage pathways and implant migration that can be caused by an insufficient fit with the aorta.

As used herein, adapted for communication, communicating, or similar terms refer to any means, structures, or methods for establishing an operational association between two elements of the system. Similarly, engaging, adapted to engage, or similar terms refer to means, structures, or methods for contacting a first component, structure, or portion thereof with a second component, structure, or portion thereof. Exemplary structures are shown in the Figures. Typically, all of these terms and phrases refer to at least one structure in or on a first component configured to engage a complementary structure in or on a second component, and the use of these inter-engaging features to link a first prosthesis or component with a second prosthesis or component. The engagement or communication may be matingly (e.g., permanent) and/or releasably (e.g., temporary). In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another prosthesis. As used herein, connector refers to any structure used to form a joint or to join itself to another component or portion thereof. These connectors or connections establish a fluid flow path through various elements of the apparatus, assembly, or system. In a preferred embodiment of the invention, the system is intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, e.g., referring to a position farthest from the beginning; in human anatomy, this term is commonly equivalent to caudal or inferior. Proximal is used in accordance with its ordinary dictionary definition, e.g., referring to a position nearest the beginning; in human anatomy, this term is commonly equivalent to cranial or superior. The terms distal and proximal are intended to convey opposite ends or portions of a device, channel, element, or structure. In relation to a fluid flow path, distal will typically refer to a downstream location in the fluid flow path, and proximal will typically refer to an upstream location, unless otherwise specifically noted. Anatomically, distal generally refers to "away from the heart" and proximal generally refers to "toward the heart."

A system for treating an aortic aneurysm according to the present invention typically includes a first prosthesis or stent gasket and at least one second prosthesis. In preferred embodiments of the invention, the components of the system are delivered intraluminally to the site of the aneurysm using a catheter or the like. One skilled in the art will therefore recognize that it is beneficial to deliver the components of the system in a closed or first position, and to deploy the component in its functional location by expanding the component into an open or second position.

Each of the components of the system will now be described in more detail. Any references to the Figures will be used to illustrate one or more exemplary embodiments of the invention, without intending to limit the invention thereby.

System

A system according to the present invention may include one or more prostheses. In the exemplary system shown in FIG. 1, the system includes a first prosthesis 10 and two second prostheses 11a and 11b, which, in combination, bypass an aneurysm 100. In preferred embodiments of the invention, a proximal portion of the system may be positioned in a portion 101 of an artery upstream of the aneurysm 100, and a distal portion of the system may be positioned in a downstream portion 102 of the artery or a different artery.

A prosthesis in accordance with the present invention includes a support, stent, or lattice of interconnected struts defining an interior space having an open proximal end and an open distal end. The lattice also defines an interior surface and an exterior surface. The interior and/or exterior surfaces of the lattice, or a portion of the lattice, may be covered by or support at least one covering material, such as a foam or graft material.

As noted in more detail below in relation to specific system components, some prostheses of the present invention may be configured to seal and/or anchor the system in place, and/or to receive and position other prostheses. Typically these prostheses do not themselves define a fluid flow path. Other prostheses may be configured to define at least one fluid flow path. Typically, these prostheses define a channel or the like through which fluid, such as blood, flows. This channel or fluid flow path typically begins upstream of, or in an upstream portion of, a component of the system. In some embodiments of the invention, the fluid flow path bypasses the aneurysm.

Figure 8:
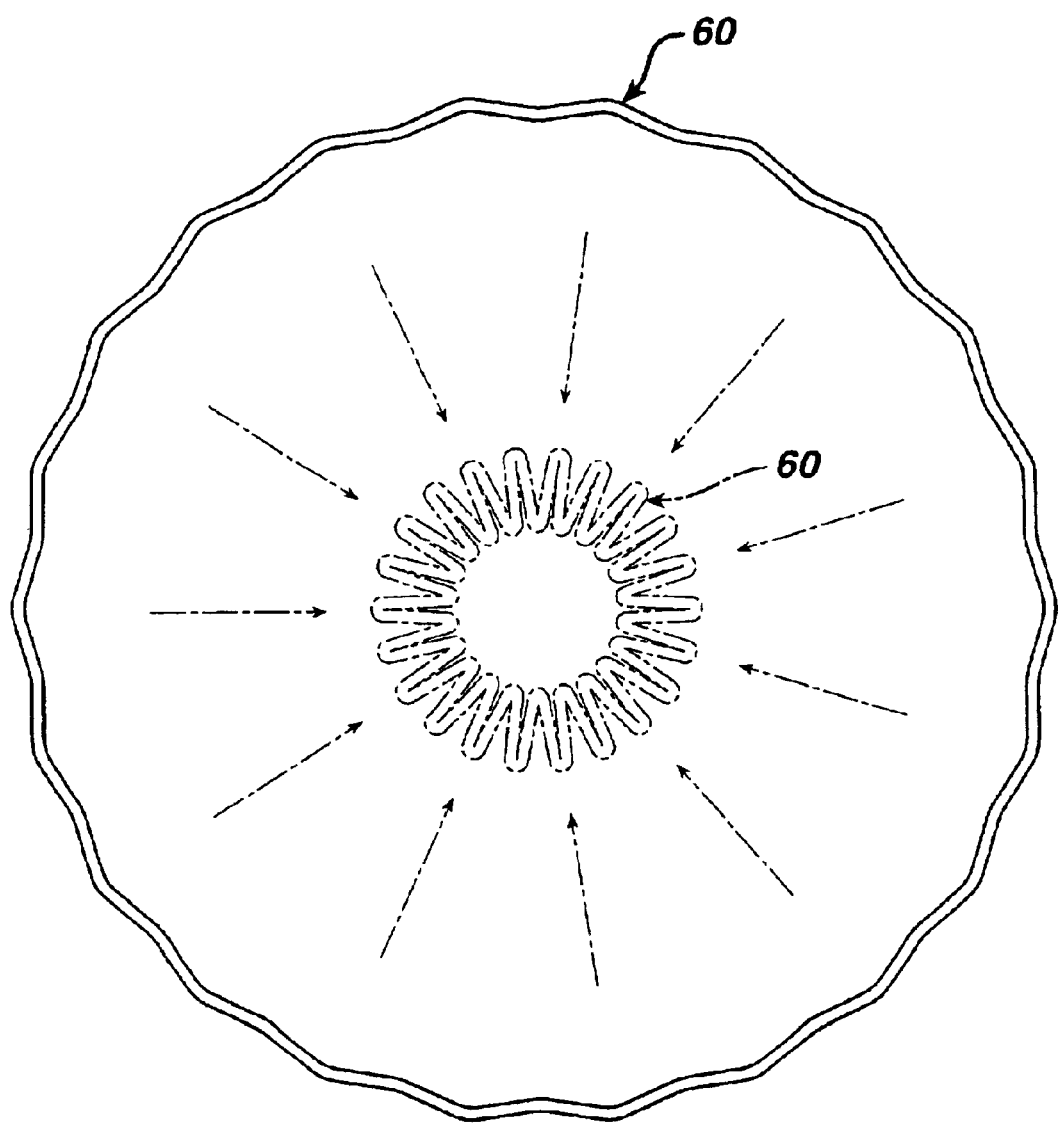
FIG. 8 is an end view of the graft material illustrating the graft material in its unexpanded or crimped configuration and in its fully expanded configuration.

In preferred embodiments of the invention, a prosthesis is moveable between an expanded or inflated position and an unexpanded or deflated position, and any position therebetween. An exemplary embodiment of this feature of the invention is shown in FIG. 8 and is intended to generically illustrate a stent or stent graft in its expanded or unexpanded position. In some embodiments of the invention, it may be desirable to provide a prosthesis that moves only from fully collapsed to fully expanded. In other embodiments of the invention, it may be desirable to expand the prosthesis, then collapse or partially collapse the prosthesis. Such capability is beneficial to the surgeon to properly position or re-position the prosthesis. In accordance with the invention, the prosthesis may be self-expanding, or may be expandable using an inflatable device, such as a balloon or the like.

An exemplary embodiment of a system for treating an abdominal aortic aneurysm according to the present invention is shown in FIG. 1. For the purpose of this embodiment, the system is deployed in the infrarenal neck 101 of the abdominal aorta, upstream of where the artery splits into first and second common iliac arteries. FIG. 1 shows first prosthesis or stent gasket 10 positioned in the infrarenal neck 101; two second prostheses, 11a and 11b, the proximal ends of which matingly engage a proximal portion of stent gasket 10, and the distal ends of which extend into a common iliac artery 1 or 2. As illustrated, the body of the prosthesis forms a conduit or fluid flow path that passes through the location of the aneurysm 100. In preferred embodiments of the invention, the components of the system define a fluid flow path that bypasses the section of the artery where the aneurysm is located.

These and other features of the prosthetic devices and systems of the present invention will be described in more detail below.

First Prosthesis or Sealing Prosthesis

The first prosthesis includes a support matrix or stent that supports a sealing material or foam, at least a portion of which is positioned across a biological fluid flow path, e.g., across a blood flow path. In preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed of a wide variety of materials, may be configured in a wide variety of shapes, and their shapes and uses are well known in the art. Exemplary prior art stents are disclosed in U.S. Pat. No. 4,733,665 (Palmaz); U.S. Pat. No. 4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the shape may be generally cylindrical, elliptic, oval, rectangular, triangular, or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials are composed of a biodurable and biocompatible material, including but are not limited to, open cell foam materials and closed cell foam materials. Exemplary materials include polyurethane, polyethylene, polytetrafluroethylene; and other various polymer materials, preferably woven or knitted, that provide a flexible structure, such as Dacron®. Highly compressible foams are particularly preferred, preferably to keep the crimped profile low for better delivery. The sealing material or foam is preferably substantially impervious to blood when in a compressed state.

The sealing material may cover one or more surfaces of the stent i.e., can be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In preferred embodiments of the invention, the sealing material stretches or covers a portion of the proximal end of the stent and along at least a portion of the outside wall of the stent.

In some embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In preferred embodiments of the invention, the sealing material is a foam cover that has a single hole.

The sealing material may be attached to the stent by any of a variety of connectors, including a plurality of conventional sutures of polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing first prosthesis may be deployed within the infrarenal neck, between an abdominal aortic aneurysm and the renal arteries of a patient, to assist in repairing an abdominal aortic aneurysm.

Figure 2:
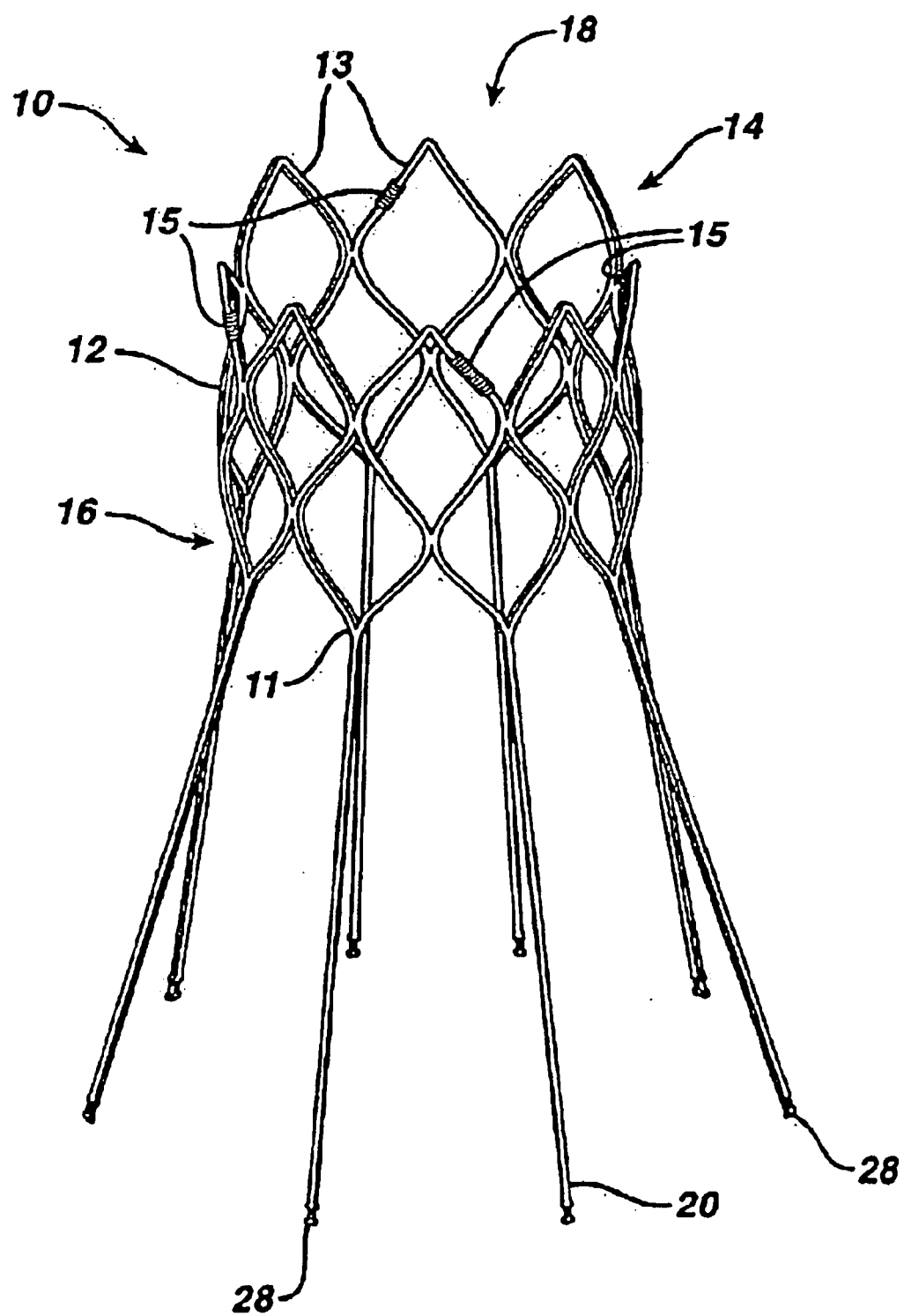
FIG. 2 is a perspective view of a stent for a first prosthesis, shown for clarity in an expanded state.
Figure 3:
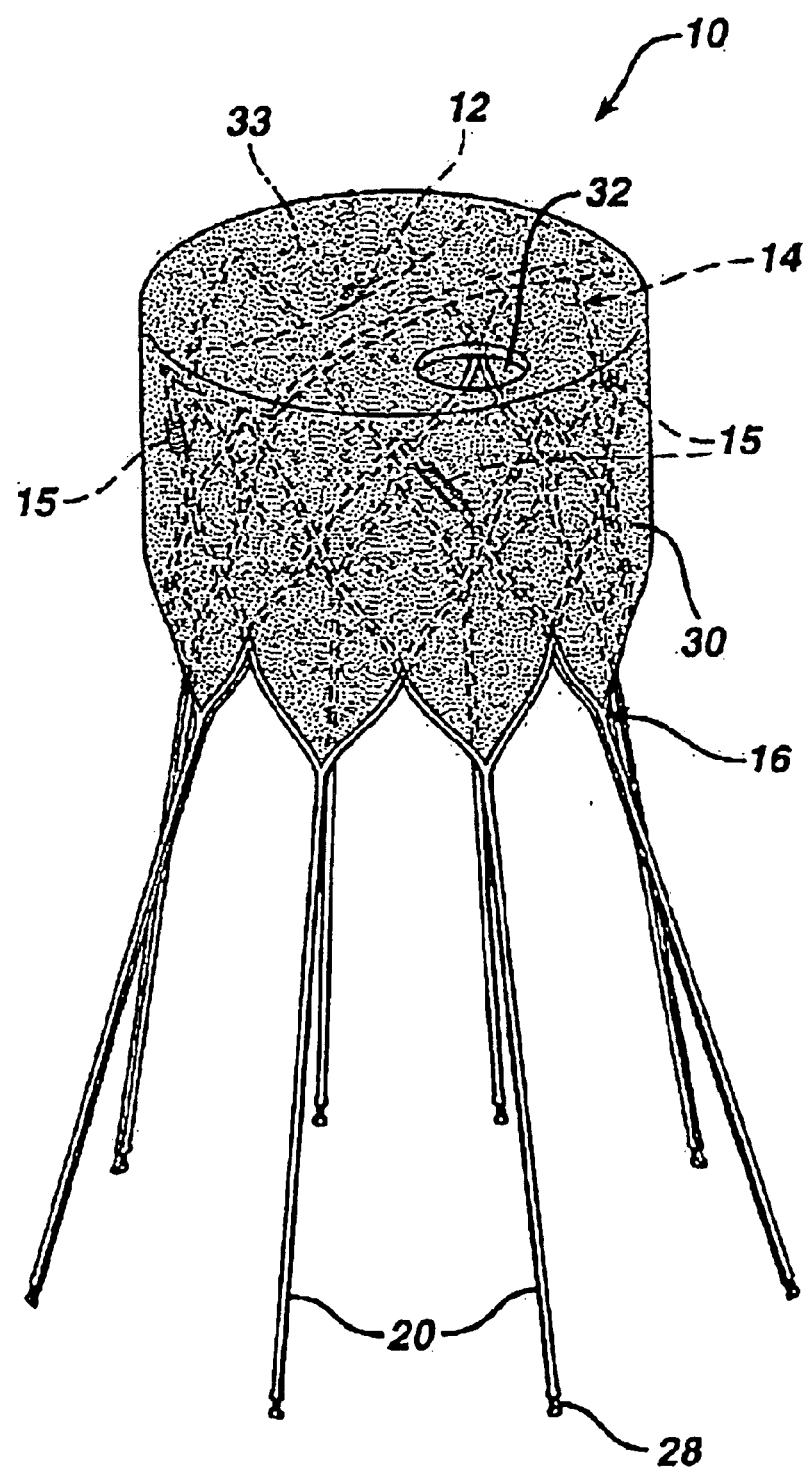
FIG. 3 is a perspective view of a first prosthesis having a stent covered by a gasket material.

FIGS. 1-3 show an exemplary sealing prosthesis 10 of the present invention. Sealing prosthesis 10 includes a substantially cylindrical self-expanding lattice, support, or stent 12, typically made from a plurality of interconnected struts 13. Stent 12 defines an interior space or lumen 18 having two open ends, a proximal end 14 and a distal end 16. One or more markers 15 may be optionally disposed in or on the stent between the proximal end 14 and the distal end 16.

Stent 12 may further include at least two, but preferably eight (as shown in FIG. 2) spaced apart longitudinal legs 20. Preferably, there is a leg extending from each apex 11 of diamonds formed by struts 13. At least one leg, but preferably each leg, includes a flange 28 adjacent its distal end which, as is described in greater detail below, allows for the stent to be retrievable into its delivery apparatus after partial or nearly full deployment of member 12 so that it can be turned, or otherwise repositioned for proper alignment.

FIG. 3 shows the sealing material 30 covering the proximal end of the first prosthesis or stent gasket 10. In the exemplary embodiment shown in FIG. 3, sealing or first prosthesis 10 includes a sealing material 30 having a first opening or hole 32 and a second opening or slit 33. The gasket material covers at least a portion of the interior or exterior of the stent, and most preferably covers substantially all of the exterior of the stent. For example, gasket material 30 may be configured to cover stent 12 from the proximal end 14 to the distal end 16, but preferably not covering longitudinal legs 20.

The sealing material helps impede any blood trying to flow around bypass prostheses 11a and 11b after they have been deployed (as shown in FIG. 1), and from flowing around the stent gasket or first prosthesis itself. For this embodiment, sealing material 30 is a compressible member or gasket located along the exterior of the stent 12 and at least a portion of the interior of the stent 12.

Second Prosthesis

The second prosthesis is a bypass conduit or the like that is typically deployed in an arterial passageway upstream of an aneurysm, and establishes a fluid flow path through the system or a portion thereof. In some embodiments of the invention, the second prosthesis defines a fluid flow path that passes through the arterial segment having the aneurysm, e.g., bypassing the aneurysm. In these embodiments of the invention, the second prosthesis extends from a healthy portion of the artery, through the arterial segment having the aneurysm, and into another healthy portion of the artery or another artery. The second prosthesis functions to bypass the portion of the conduit containing the aneurysm, and to properly position and/or anchor the proximal end of the system in an artery. In some embodiments of the invention, the second prosthesis defines a fluid flow path from one portion of the system, e.g., a proximal portion or end, to another portion, e.g., a distal portion or end, or an intermediate portion.

The second prosthesis may also include one or more structures for positioning and anchoring the second prosthesis in the artery or in the first prosthesis. In a preferred embodiment of the invention, the second prosthesis is adapted to engage the first prosthesis.

One or more markers may be optionally disposed in or on the second prosthesis between the proximal end and the distal end. Preferably, two or more markers are sized and/or positioned to identify a location on the prosthesis, or to identify the position of the prosthesis, or a portion thereof, in relation to an anatomical feature or another system component. In preferred embodiments of the invention, fluoroscopically identifiable sutures or staples are used; these sutures or staples may also attach the graft material to the stent to form the second prosthesis.

FIGS. 1 and 4–6 show an exemplary second or bypass prosthesis 11a, b of the present invention. Second prosthesis 11a, b includes a substantially cylindrical self-expanding lattice, support, or stent 40, typically made from a plurality of interconnected struts 44. Lattice 40 defines an interior space having two open ends, a proximal end 41 and a distal end 42. The interior and/or exterior surfaces of lattice 40 may be covered by or support at least one graft material 60.

The second prosthesis typically includes a support matrix or stent that supports a graft material. One end of the second prosthesis is typically adapted to engage one or more portions of first prosthesis. In preferred embodiments of the invention, the proximal end of the second prosthesis is adapted to matingly engage a proximal portion of first prosthesis. The second prosthesis may optionally include at least one attachment structure on its distal end for engaging and securing the prosthesis in a portion of an artery downstream of the aneurysm. These and other features of the second prosthesis will be described in more detail below.

Extension Prosthesis

An extension or third prosthesis according to the present invention is a stent covered with a graft material, as described above, and may be adapted to provide a fluid flow path. In some embodiments of the invention, the extension prosthesis is configured to provide a fluid flow path upstream from the system. In these embodiments of the invention, the extension prosthesis is configured to engage a portion of the first prosthesis. If the extension prosthesis is being used to treat an abdominal aortic aneurysm, the fluid flow path upstream of the system may be infra-renal, trans-renal, or supra-renal.

In some embodiments of the invention, the extension prosthesis is configured to extend an existing fluid flow path, e.g., extend the fluid path provided by the second prosthesis. For example, the extension prosthesis may be configured to provide a fluid flow path downstream from the system. In these embodiments of the invention, the extension prosthesis is configured to engage a portion of the second prosthesis, and extends from the second prosthesis, through the arterial segment having the aneurysm, and into another healthy portion of the artery or another artery. The extension prosthesis may function to bypass the portion of the artery containing the aneurysm, and/or to properly position and/or anchor the distal end of the system in an artery. In some embodiments of the invention, the extension prosthesis defines a fluid flow path from one portion of the system, e.g., a proximal portion or end, to another portion, e.g., a distal portion or end, or an intermediate portion.

The extension or third prosthesis may also include one or more structures for positioning and anchoring the extension prosthesis in the artery or in the second prosthesis. In a preferred embodiment of the invention, the extension prosthesis is adapted to engage the second prosthesis.

One skilled in the art will recognize that an extension prosthesis configured according to the present invention may also be used to support, repair, or reinforce another prosthesis, such as a second prosthesis. For example, if a second prosthesis forms a kink, it may be desirable to position an extension prosthesis within the second prosthesis, and radially expand the extension prosthesis to thereby strengthen and/or repair the kink in the second prosthesis to cover the kinked area.

In accordance with the present invention, the extension prosthesis may be variously configured. For example, the extension prosthesis may be configured as described above for the second prosthesis.

In preferred embodiments of the invention, the stent of the extension prosthesis is a collapsible, flexible, and self-expanding lattice or matrix formed from a metal or metal alloy, such as nitinol or stainless steel. More preferably, the stent is a tubular frame that supports a graft material. The shape may be generally cylindrical, elliptic, oval, rectangular, triangular, or any other shape. Furthermore, the shape may change or be deformable as a consequence of various forces that may press against the stent or prosthesis. In preferred embodiments of the invention, the distal and proximal ends of the stent are a different diameter than an intermediate portion of the stent. For example, one or both ends may be flared. As will be described in more detail below, in the most preferred embodiments of the invention, both ends are flared, and one end has a greater diameter or cross section than the other end.

The graft material supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The graft material may cover one or more surfaces of the stent i.e., can be located along an interior or exterior wall, or both, and preferably extends from one flared end to the other. In the most preferred embodiments of the invention, the portion of the stent on both ends that includes one or more connectors is not covered by graft material.

The graft material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit, and staples. In preferred embodiments of the invention, the graft material is attached to the stent using a number of sutures, e.g., six sutures at or near each end.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

As noted above, the extension prosthesis may be engaged, preferably matingly engaged, to another prosthesis in the system in order to provide a fluid flow path. The extension prosthesis is preferably configured to form a fluid tight seal with the other prosthesis. Any configuration and/or assembly of elements that achieves a fluid-tight seal may be used. For example, the first and/or second prosthesis may include a gasket that spans the lumen, the gasket having an aperture configured to receive an end portion of the extension prosthesis. An exemplary gasket configuration is described above for the first prosthesis. Such a gasket preferably seats and sealingly engages the extension prosthesis. Other examples of a fluid tight seal engagement between the extension prosthesis and another prosthesis includes, but is not limited to, a butt joint, a slip joint, or a slip union.

Further, the engagement between the extension prosthesis and the other prosthesis may be formed by gasket material, graft material, a portion of the stent of one or both prostheses, or combinations thereof. For example, in some embodiments of the invention, it may be desirable to provide a second prosthesis having a stent whose shape memory is inwardly focused, i.e., toward the lumen of the prosthesis, and an extension prosthesis stent whose shape memory is outwardly focused, i.e., away from or expanding the lumen of the prosthesis.

In preferred embodiments of the invention, the extension or third prosthesis sealingly engages a first or second prosthesis using an interference fit. The seal may be formed by a flared portion of the extension prosthesis engaging a tapered portion of another prosthesis, or any other nesting configuration. One skilled in the art will recognize that by configuring the second prosthesis in relation to the configuration of the extension prosthesis, various arrangements may provide a fluid tight seal. Also, the seal may be formed in a discrete section of engagement between a portion of the extension prosthesis and the other prosthesis, or the seal may be gradual, e.g., formed gradually over a longitudinal length of contact between the extension prosthesis and the other prosthesis.

In preferred embodiments of the invention in which the extension or third prosthesis sealingly engages a second prosthesis, the engagement is a frictional engagement in which a sufficient length of the extension prosthesis contacts the inner wall of the second prosthesis. Any length is sufficient if it results in a fluid tight seal, preferably a fluid tight seal when the system is fully deployed in the artery. In addition, the length should be sufficient to compensate for any potential migration. It has been found that a thirty to fifty mm length overlap between the extension prosthesis and the second prosthesis forms a fluid tight seal, but the invention should not be limited to a specific length of overlap.

It has also been found that some types of staples typically used in the prior art to connect one tubular structure or prosthesis to another may result in an abrasive engagement between the two prostheses, abrasion that may lead to earlier and/or deleterious wear. In preferred embodiments of the present invention, the engagement between an extension prosthesis and another prosthesis should involve non-abrasive contact.

In accordance with the present invention, the most preferred configuration of an extension prosthesis includes graft material covering a central portion of the prosthesis, i.e., connectors on the stent on both ends are exposed or uncovered; and one end of the extension prosthesis is flared or has a larger diameter than its opposite end. Such a configuration is particularly well suited for use at either the upstream end of the system, first prosthesis, or second prosthesis, or the downstream end. For example, if the extension prosthesis is being used to extend a downstream portion of the system or the second prosthesis, the flared or larger diameter end of the extension prosthesis is the proximal or upstream end, and is delivered first. If the extension prosthesis is being used to extend an upstream portion of the system, the first prosthesis, or the second prosthesis, the smaller diameter end of the extension prosthesis is the proximal or upstream end, and is delivered first.

Figure 16:
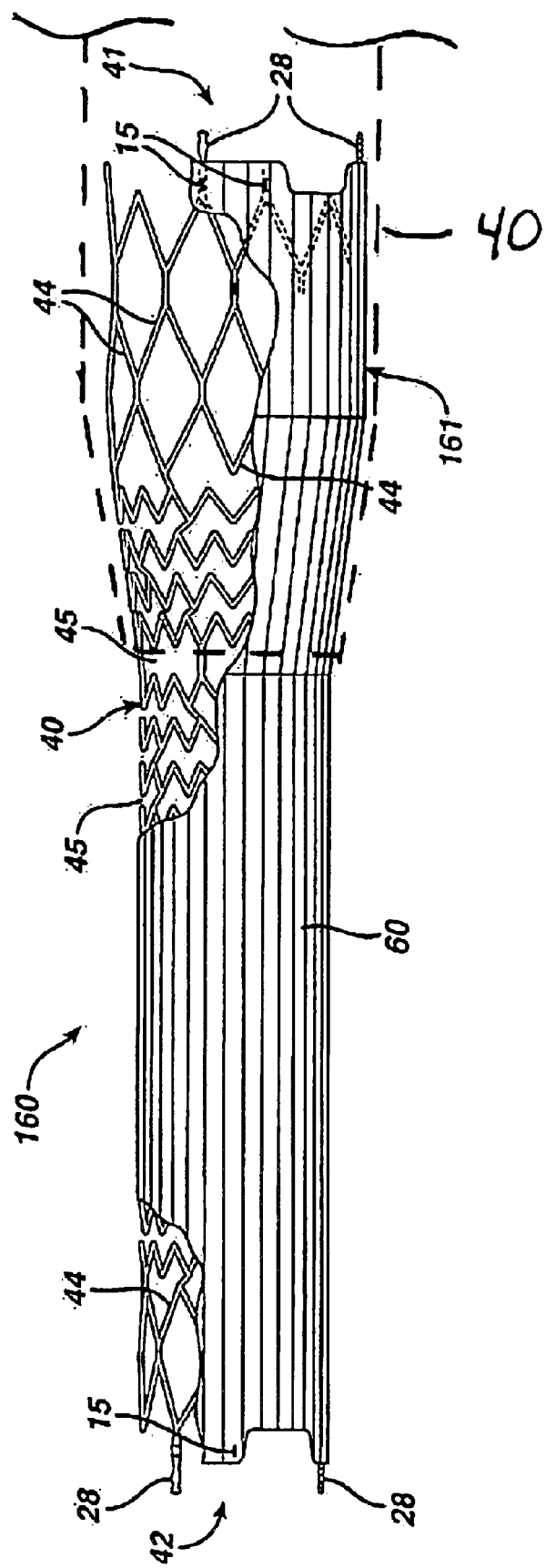
FIG. 16 is a side elevation of a third or extension prosthesis having a stent covered by a graft material.

FIG. 16 shows an exemplary extension prosthesis 160 of the present invention. The extension prosthesis 160 typically includes a support matrix or stent 40 that supports a graft material 60. Stent 40 is a substantially cylindrical self-expanding lattice or support, typically made from a plurality of interconnected struts 44. Stent 40 defines an interior space having two open ends, a proximal end 41 and a distal end 42.

FIG. 16 also illustrates an alternative embodiment of a stent 40 for second prosthesis 11a, b, as well as extension prosthesis 160. In an intermediate portion of the stent, interconnected struts 44 may be unattached at exemplary positions 45 in order to increase the flexibility of the stent and to increase kink resistance. Other configurations may be adopted to achieve such a structure having greater flexibility. Additional configurations are described below.

In the illustrated embodiment, proximal end 41 is adapted to engage one or more portions of second prosthesis 11a, b (illustrated in FIG. 1), typically an interior wall of prosthesis 11a, b. In preferred embodiments of the invention, a distal portion of second prosthesis 11a, b is adapted to matingly engage a proximal portion 161 of extension prosthesis 160. The distal end 42 is adapted to engage, contact, or be positioned in an artery.

In adapting the extension prosthesis to engage the second prosthesis, the proximal end of the extension prosthesis may be flared or unflared. In a most preferred embodiment of the invention, the proximal end of extension prosthesis 160 may be slightly flared outwardly, preferably to more easily effect the mating engagement between the second prosthesis and the extension prosthesis. It is intended that the length of the flared portion of the extension prosthesis should approximate the length of overlap between the distal end of the second prosthesis and the proximal end of the extension prosthesis.

In preferred embodiments of the invention, on the downstream end of a prosthesis that provides a fluid flow path, the graft material may be shaped to conform to the pattern of struts supporting the graft material. For example, the downstream edge of graft material 60 is preferably fully supported by the underlying stent. Such a configuration may be desirable to prevent unsupported sections of the graft material from folding into the lumen of the stent.

Stent

Any of the stents of the present invention form a support or lattice structure suitable for supporting a graft material. In preferred embodiments of the invention, the stent defines a channel through which a fluid, such as blood, may flow. A typical stent comprises an expandable lattice or network of interconnected struts. In preferred embodiments of the invention, the lattice is machined from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In some exemplary embodiments of the invention, the struts of the stent gasket form a matrix having diamond shapes. In the exemplary embodiment of the invention shown in FIG. 2, the matrix or struts of stent 10 are configured into a diamond shapes, preferably having approximately eight diamonds. In this exemplary embodiment of the invention, the fully expanded diamond pattern of a first prosthesis has angles of forty-five to fifty-five degrees at their distal and proximal ends. In the exemplary embodiment of the invention shown in FIG. 5, the matrix or struts of stent 40 may be configured into at least two hoops 43, each hoop 43 comprising a number of struts 44 having a diamond shape, having approximately nine diamonds. A second prosthesis, such as second prosthesis 40, may further include a zigzag shaped ring 50 for connecting adjacent hoops to one another. The zigzag shaped rings may be formed from a number of alternating struts 52, wherein each ring has fifty-four struts.

The diamond pattern for the anchors, as well as the other hoops, provide the hoops with radial and longitudinal stiffness. The longitudinal strength provides for better mechanical fixation of stent 40 to a graft material (described below). The radial strength provides the proximal hoop 45a with better attachment and sealing to the gasket material, and provides the distal hoop 45b with better fixation and sealing to the arterial wall. Further, the distal hoop may be flared, and may be exposed after the graft material has been attached to the stent.

In one preferred embodiment, the proximal and distal hoops have greater radial and longitudinal strength than the hoops therebetween. This creates a stent graft having stiff ends for anchoring, but a more flexible body for navigation through the vasculature. The stiffer ends can be accomplished by changing the dimensions of the struts for the end hoops, or by varying the heat treatment of the end hoops during manufacture. The rings allow the stent to bend more easily, and generally provide for more flexibility when the stent is being delivered through a tortuous vessel. When a non-compliant graft is attached to a stent, the strength of the diamond hoops scaffolds any graft folding into the blood flow lumen, while maintaining a tight kink radius.

In accordance with some embodiments of the present invention, the proximal and/or distal end of a stent may include one or more anchors and/or one or more struts of the stent configured into an anchor. One or more anchors, commonly referred to as recapture legs, may also be configured to releasably engage a delivery device, such as a catheter, or a portion thereof.

In the exemplary embodiments of the invention in which an extension prosthesis is matingly engaged to a second prosthesis, it has been found advantageous to provide an interlocked mating engagement between the two prostheses. The interlock configuration may be achieved by a variety of structures. In a preferred embodiment, the proximal end of the stent of the extension prosthesis may include free or open diamond shapes, the unattached struts of which can interlock with closed diamond shapes on a distal end of the bypass prosthesis.

Figure 15:
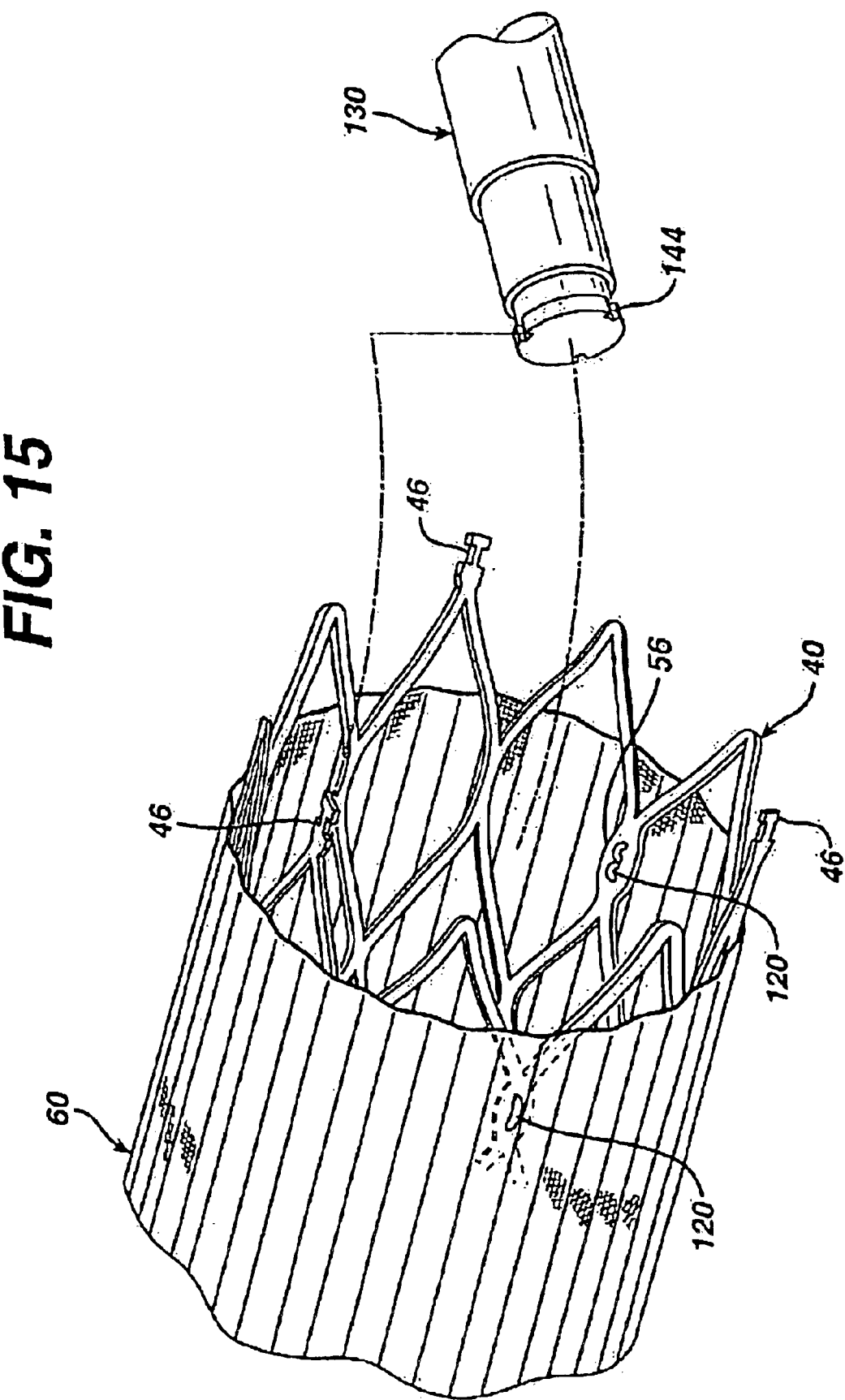
FIG. 15 is a partial, exploded perspective view of the proximal end of a second prosthesis of the present invention illustrating an anchoring and delivery system according to the invention.

The distal end of the stent is preferably configured to engage a complementary structure on a delivery device, such as a catheter or a portion thereof. For example, the distal end of the stent may include one or more keys that engage, preferably releasably engage, a corresponding latch on the catheter. An exemplary configuration is shown in FIG. 15. It is intended that the invention should not be limited by the precise structures used to engage the stent to the delivery device.

In the exemplary embodiments of the invention shown in FIGS. 1–3 and 15, the stent may include one or more anchors 28, 46 configured to engage a corresponding structure on a delivery device 130. In accordance with the present invention, the delivery apparatus may include a collar having one or more grooves or the like adapted to releasably engage one or more complementary structures on a stent or prosthesis of the present invention. For example, the delivery apparatus 130 shown in FIG. 7 includes eight grooves 144 to configure the delivery device to releasably engage both the first prosthesis 10 in FIG. 1 (having eight anchors 28 as illustrated in FIG. 2), and the delivery apparatus 130 shown in FIG. 15 includes three grooves 144 to configure the delivery device to releasably engage the second prosthesis 11a, b in FIG. 15 (having three anchors 46). Such an anchor/delivery device configuration is particularly suited to partially deploying a prosthesis of the present invention, and to position or re-position the prosthesis.

Any of the stents of the present invention may be formed of any material suitable for functioning in vivo as a support for graft material. A stent of the present invention may be formed from a wide variety of materials, all of which are well known to those skilled in the art. In some embodiments of the invention, the stent is formed from a metal or metal alloy. In preferred embodiments of the invention, the stent is formed from superelastic Nickel Titanium alloys (Nitinol). Descriptions of medical devices which use such alloys can be found in U.S. Pat. No. 4,665,906 and European Pat. Application EP 0928606, both of which are hereby incorporated herein by reference. A stent according to the invention is preferably laser cut from a tubular piece of nitinol and thereafter treated so as to exhibit superelastic properties at body temperature. In preferred embodiments of the invention, the stent material is expandable or collapsible, i.e., moveable from a first closed position to a second open position, or vice versa.

Graft Material

An inner or outer surface of a stent of the present invention may be covered by or support a graft material. Graft material 60 (FIGS. 4, 6, 8, 10, 11, 13, 14, 15 and 16) can be made from any number of materials known to those skilled in the art, including woven polyester, Dacron®, Teflon®, polyurethane, porous polyurethane, silicone, polyethylene terephthlate, expanded polytetrafluoroethylene (ePTFE) and blends of various materials.

In some embodiments of the invention, it may be desirable to incorporate a biodegradable, or degradable material, such as albumin, collagen, or any type of collagen. A graft material that is biodegradable would erode or dissolve over time; it is believed that the eroding graft material may be replaced by one or more biofusion constituents.

The graft material may be variously configured, preferably to achieve predetermined mechanical properties. For example, the graft material may incorporate a single or multiple weaving and/or pleating patterns, or may be pleated or unpleated. For example, the graft may be configured into a plain weave, a satin weave, include continuous longitudinal pleats, interrupted pleats, annular or helical pleats, radially oriented pleats, or combinations thereof. Alternately, the graft material may be knitted or braided. In the exemplary embodiments of the invention in which the graft material is pleated, the pleats may be continuous or discontinuous. Also, the pleats may be oriented longitudinally, circumferentially, or combinations thereof.

Figure 6:
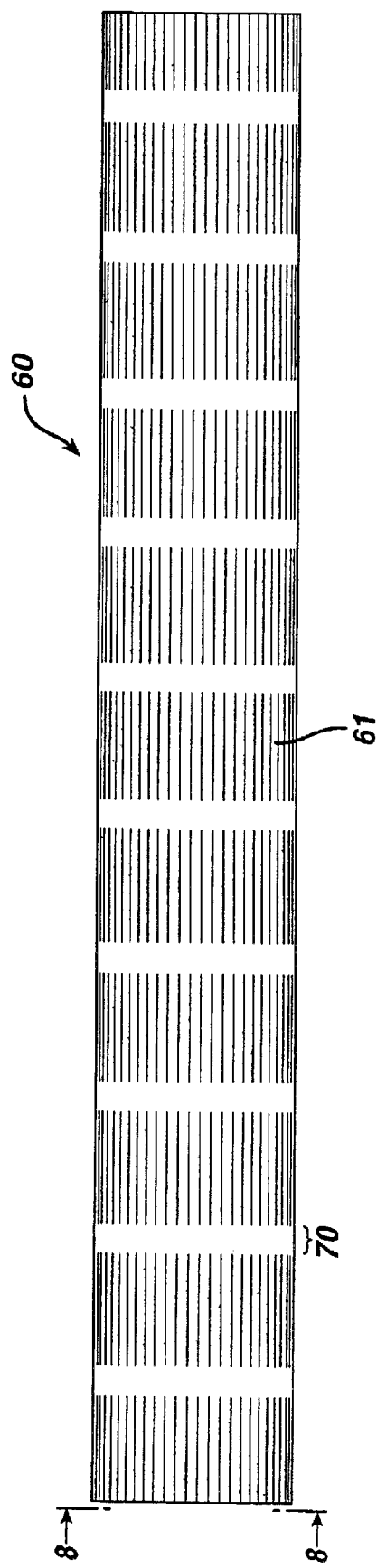
FIG. 6 is a side elevation of a longitudinally pleated graft material configured for placement on the stent of FIG. 5.

As shown in FIG. 6, graft material 60 may include a plurality of longitudinal pleats 61 extending along its surface, generally parallel to the longitudinal axis of the prosthesis. As shown in FIG. 8, the pleats allow the prosthesis to collapse around its center, much as it would be when it is delivered into a patient. As illustrated, the pleats come together as a series of radially oriented regular folds that pack together efficiently. This provides a relatively low profile delivery system, and provides for a controlled and consistent deployment therefrom. It is believed that this configuration minimizes wrinkling and other geometric irregularities. Upon subsequent expansion, the prosthesis assumes its natural cylindrical shape, and the pleats or folds uniformly and symmetrically open.

In addition, pleats 61 help facilitate stent graft manufacture, in that they indicate the direction parallel to the longitudinal axis, allowing stent to graft attachment along these lines, and thereby inhibiting accidental twisting of the graft relative to the stent after attachment. The force required to push the stent-graft out of the delivery system may also be reduced, in that only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

As shown in FIG. 6, the graft material may also include one or more, and preferably a plurality of, radially oriented pleat interruptions 70. The pleat interruptions are typically substantially circular and are oriented perpendicular to longitudinal axis. Pleat interruptions 70 allow the graft and prosthesis to bend better at selective points. This design provides for a graft material that has good crimpability and improved kink resistance (see also FIG. 4).

The graft material as described above is preferably highly compressible, which also promotes a low crimped profile for better delivery characteristics.

In accordance with the present invention, the graft material may be impervious or substantially impervious to the flow of blood, or may be porous. A graft material is impervious if it prevents blood from passing through the graft material on contact with blood or after the graft material is saturated with blood. Choice of the flow characteristics of a graft material are well known to those skilled in the art, and are tied in part to the intended function of the prosthesis or portion of the prosthesis. For example, it may be desirable for the graft material that forms the cover of the first prosthesis to be impervious or substantially impervious to the flow of blood. Alternately, it may be desirable for a graft material to be porous or partially porous to promote biofusion.

In addition, it is preferable that the gasket member be substantially impervious to the flow of blood, at least when in a partially compressed state. When used throughout for the present invention, materials which are substantially impervious to the flow of blood include materials which become substantially impervious to the flow of blood after being saturated with blood.

A graft material may be attached to a stent or to another graft material by any number of structures or methods known to those skilled in the art, including adhesives, such as polyurethane glue; a plurality of conventional sutures of polypropylene, Dacron®, or any other suitable material; ultrasonic welding; mechanical interference fit; and staples.

As stated above, a stent preferably has a graft member attached thereto. The graft member covers at least a portion of the interior or exterior of the stent, and most preferably covers substantially all of the exterior of the stent. In some exemplary embodiments of the invention, prosthesis 11a, b includes graft material 60 that covers only a portion of the distal end 42 of matrix 40. See, for example, FIG. 4.

In accordance with the present invention, it may be highly desirable to provide a graft material that limits or eliminates the amount of blood that passes between the graft and the arterial wall, to provide a catheter-delivered graft or prosthesis that extends through a longer portion of an artery, to improving the anchoring mechanisms between two prostheses, to improving the anchoring mechanism between the prosthesis and the arterial wall or an interluminal cavity within an artery, and to improve the fluid dynamic and performance characteristics of the implanted prosthesis.

Marker

As noted above, a stent and/or prosthesis of the present invention may include one or more markers. One skilled in the art will recognize that one or more markers may be positioned on the stent, the graft material, or on the prosthesis. In preferred embodiments of the invention, the markers are used to identify the position of the stent or prosthesis in relation to a body part and/or in relation to another stent or prosthesis, and/or to identify the position of one part of the prosthesis relative to another part. In most preferred embodiments of the invention, the marker(s) is used to identify a position in vivo.

As shown in FIGS. 2 and 3, a stent, such as stents 12 and/or 40, preferably includes one or more radiopaque markers 15. Exemplary materials for forming markers include but are not limited to tantalum, platinum, iridium, and gold. As shown, markers 15 are coils of radiopaque metal, wrapped around the struts of the stent. Markers 15 are preferably made from 0.0075 inch diameter tantalum (Ta) wire wrapped tightly around the struts.

The number, location, and size of the markers may vary, and the markers may be used alone or in combination to identify the position of a particular portion of the prosthesis. For example, a proximal marker adjacent aperture 32 may be about 5 mm long and the proximal marker adjacent hole 33 may be about 2 mm long. Also, two distal markers may be one hundred eighty degrees apart, and a proximal marker may be positioned equidistant from each of the distal markers. In this exemplary configuration, the proximal marker then aids proper rotational positioning of the device.

In connection with an extension prosthesis 160 (FIG. 16), it may be desirable to include a certain number of markers 15, e.g., three, near the proximal end of the prosthesis, and a different number of markers, e.g., six, a short distance proximally from the first set of markers. Such a configuration is an exemplary configuration of markers, which permits positioning the extension prosthesis properly within the second prosthesis.

Connectors

Some exemplary embodiments of a prosthesis according to the present invention may include one or more connectors. In some exemplary embodiments of the invention, the connectors are used to engage or connect one prosthesis or component to another. In some exemplary embodiments of the invention, the connectors may be used to attach the gasket material or graft material to a stent or lattice.

As noted above, one skilled in the art will recognize that a variety of materials and methodologies may be used to connect one prosthesis to another, or to attach the graft material to a stent. Exemplary connectors include but are not limited to sutures, staples, rivets, or the like. In preferred embodiments of the invention, the connector is a suture or staple, even more preferably, having a knotted or nub end. Further, a connector may be formed from a radiopaque material or a fluorescent material, each of which allow the connector to be used as a marker.

In accordance with the present invention, it may be desirable to incorporate in a prosthesis a connector adapted for use with a lattice-like stent. A first connector 54, an exemplary embodiment of which is shown in FIGS. 5 and 9–11, may be configured for use at an end portion of a stent, preferably at an end portion of a strut 44. A second connector 56, an exemplary embodiment of which is shown in FIGS. 5 and 12–14, may be configured for use at an internal portion of a stent, preferably at the junction between two struts 44.

Figure 9:
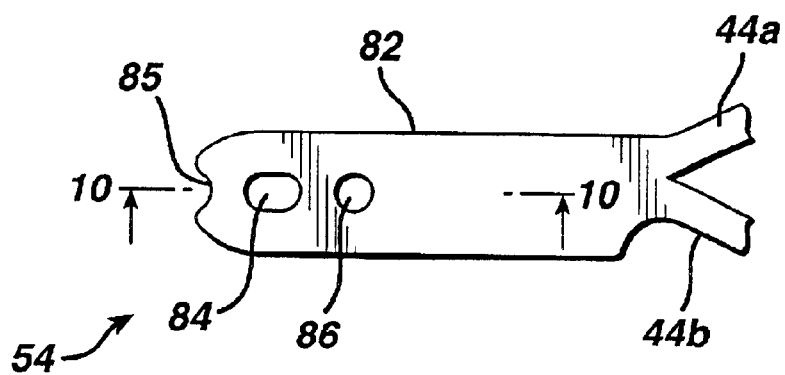
FIGS. 9 through 11 show an exemplary connector assembly of the present invention intended for use on an end portion of a stent or prosthesis.
Figure 10:
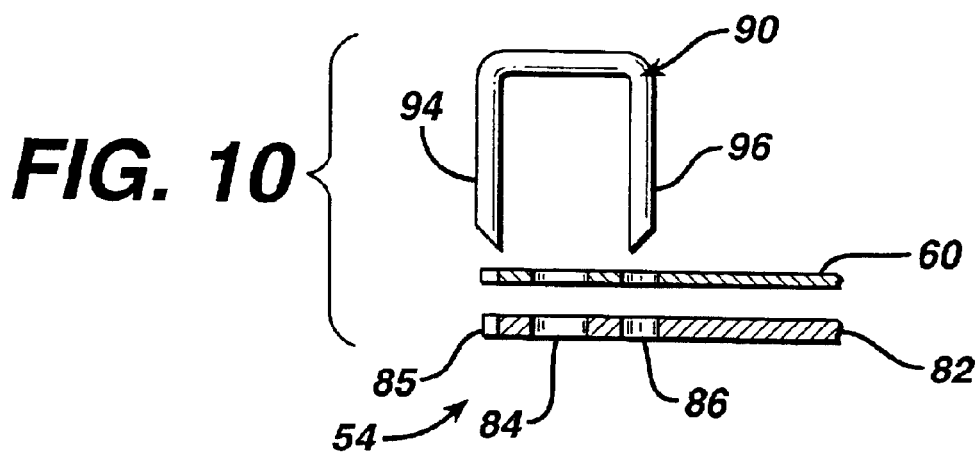
Figure 11:
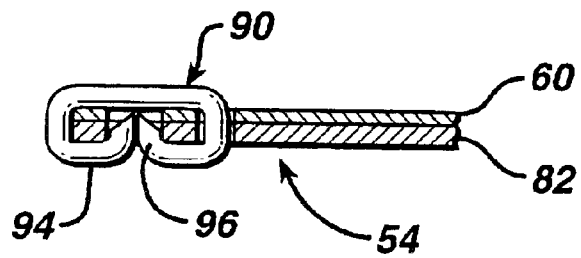
Figure 12:
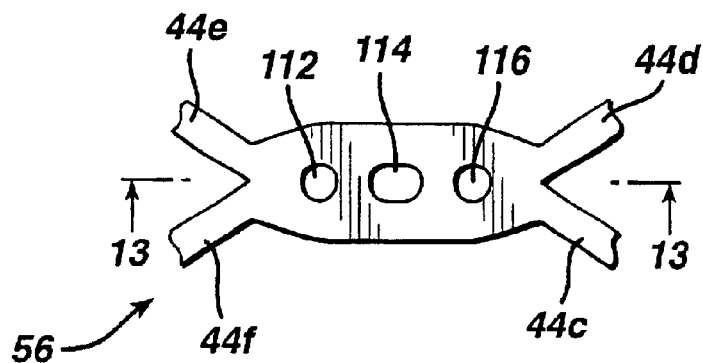
FIGS. 12 through 14 show an alternative connector assembly of the present invention intended for use on an intermediate portion of a stent or prosthesis.
Figure 13:
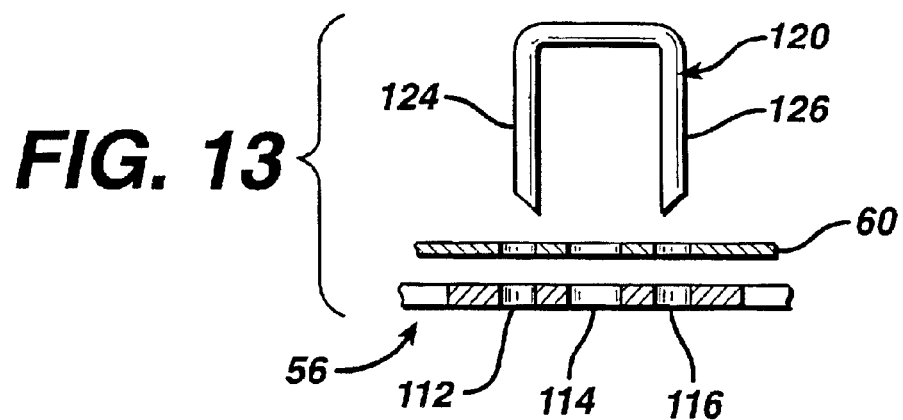
Figure 14:
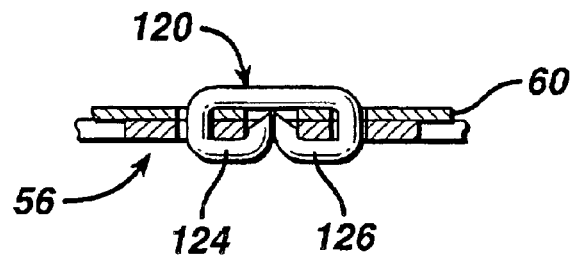

FIG. 9 shows a first connector or proximal attachment connector 54 of a stent, such as stent 40. The connector may include a tab 82 having a first aperture 84 and a second aperture 86, and preferably including a notch 85 or the like at an end opposite the strut. Tab 82 may be a separate element configured to engage a stent, or, as illustrated, may be formed of the junction of two struts 44a and 44b respectively. In the exemplary embodiment of the invention shown in FIGS. 9–11, tab 82 is configured to receive a staple 90 having a first leg 94 and a second leg 96. First aperture 84 is preferably configured to receive a tip portion of both first leg 94 and second leg 96 of staple 90. Second aperture 86 is preferably configured to allow second leg 96 to pass therethrough. In the exemplary embodiments of the invention that include a notch 85, a portion of first leg 94 opposite the tip engages or cradles in the notch 85. In use, second leg 96 passes through graft material 60, through the second aperture 86 of tab 82, and a tip portion of the second leg is bent into first aperture 84. First leg 94 of staple 90 may be positioned on connector 54 by engaging notch 85. A tip portion of the first leg is bent into first aperture 84. In one exemplary embodiment of the invention, the tip portion of the first and second legs engages and preferably penetrates graft 60. In another exemplary embodiment of the invention the tip portion of the first and second legs engages but does not penetrate the graft 60.

The structures and functions of the second connector 56 are similar or the same as those described above for the first connector. However, in a second connector configuration, the tab also includes a third aperture 112, preferably configured to allow the first leg 124 of staple 120 to pass therethrough. In use, first leg 124 and second leg 126 pass through graft material 60, first leg 124 passes through third aperture 112 and second leg 126 passes through second aperture 116, and a tip portion of each of the first and second legs are bent into first aperture 114. In one exemplary embodiment of the invention, the tip portion of the first and second legs engages and preferably penetrates graft 60. In another exemplary embodiment of the invention, the tip portion of the first and second legs engages but does not penetrate the graft 60.

In accordance with preferred embodiments of the invention, a prosthesis may be matingly engaged to another prosthesis using a connector having a nub or spherical end. Exemplary connectors for this aspect of the invention include but are not limited to a rivet, staple, suture, or combinations thereof. An exemplary connector assembly for this embodiment of the invention is shown in FIGS. 17a and 17b.

Figure 4:
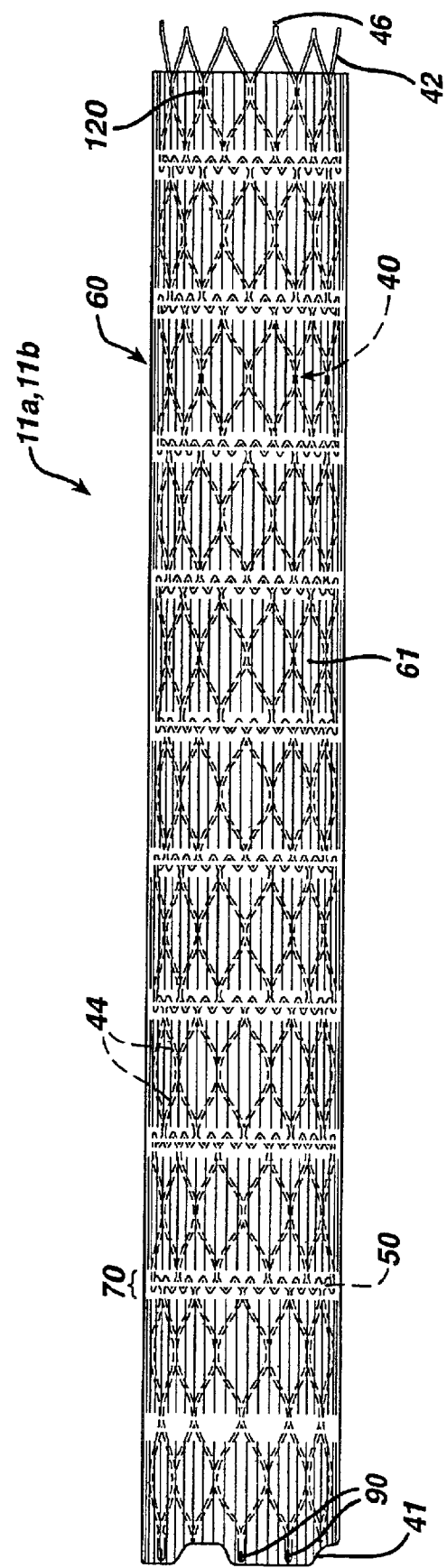
FIG. 4 is a side elevation of a second prosthesis having a stent covered by a graft material.
Figure 5:
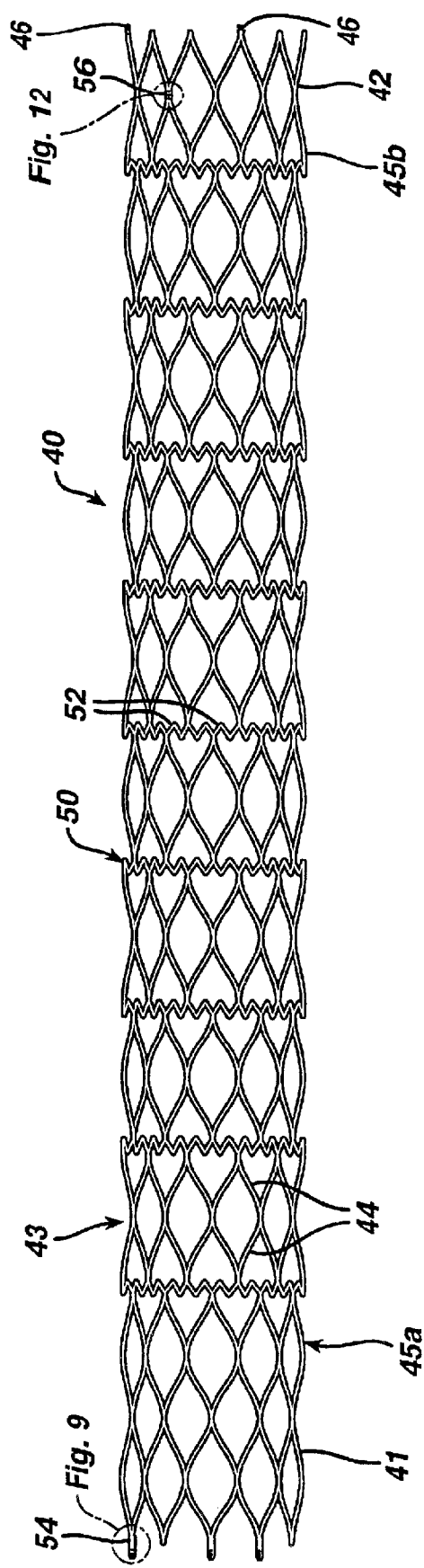
FIG. 5 is a side elevation of a stent for a second prosthesis, shown for clarity in an expanded state.
Figure 17A:
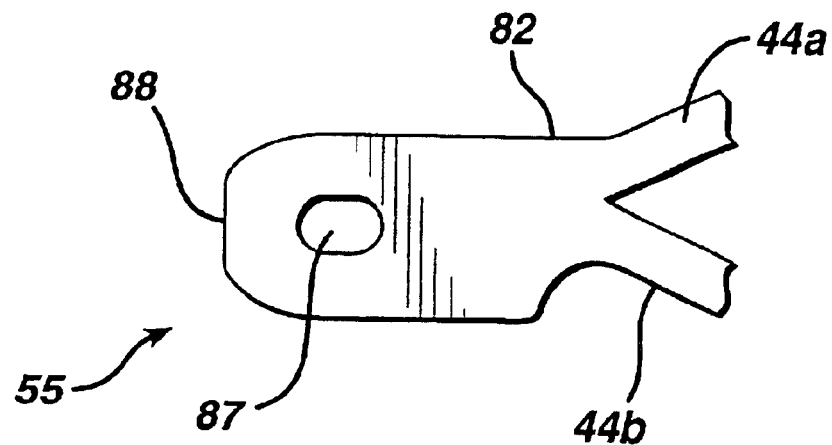
FIGS. 17a and 17b illustrate an alternative connector assembly of the present invention wherein the connector is a suture or the like having a nub or spherical end.

FIG. 17a is an exemplary distal connector on the stent 40 of second prosthesis 11a, b, as illustrated in FIGS. 4 and 5, and an exemplary proximal connector on the stent 40 of third prosthesis 160. The connector 55 is preferably formed from a tab 82 or the like at the junction of two struts, 44a and 44b. Tab 82 includes an aperture 87 near the end 88 of the tab opposite the struts, the aperture being configured to receive a rivet, suture or staple, or the like.

Figure 17B:
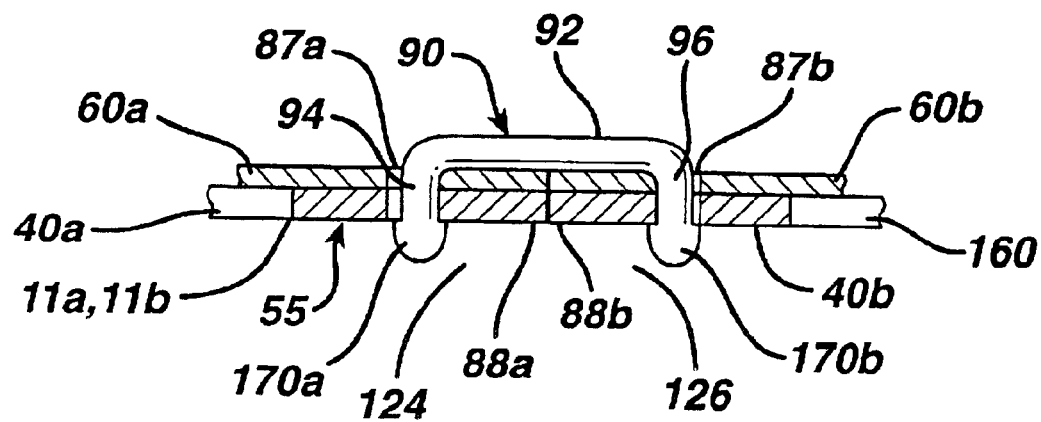

FIG. 17b shows the mating engagement of the second prosthesis 11a, b and the third prosthesis 160. As illustrated, second prosthesis 11a, b includes a distal end 88a having a graft material 60a covering an exterior surface of stent 40a. The third prosthesis 160 includes a proximal end 88b having a graft material 60b covering an exterior surface of stent 40b. After ends 88a and 88b are aligned, a portion of suture or staple 90 or the like is passed through aperture 87. In the illustrated embodiment, suture or staple 90 includes a crown 92 that bridges an exterior surface of prosthesis 11a, b and prosthesis 160. The suture or staple 90 includes a first leg 94 that passes through aperture 87a and a second leg 96 that passes through aperture 87b. Once the suture and prostheses are aligned and in place, the tip of first leg 94 and second leg 96, distal from the crown 92, and positioned on an exterior surface of stents 40a and 40b, may be configured into a nub or spherical element 170a and 170b. It should be evident to one skilled in the art that the nub should be of a larger diameter than the diameter of the aperture. In a preferred embodiment of the invention, nubs 170a and 170b may be formed by melting the respective tips.

The invention also includes an alternate exemplary embodiment for connecting the second prosthesis with the third prosthesis. In this alternate exemplary embodiment (not illustrated), apertures 87a and 87b are aligned and a rivet having two tips is passed through the aligned apertures. Each tip may then be configured into a nub or the like, as described above. In this exemplary embodiment of the invention, second prosthesis is matingly engaged to a third prosthesis using one or more rivets that are barbell shaped once the nubs are formed.

The number of connectors and staples are typically dictated by the size and structure of a particular stent; it is intended that the invention should not be limited thereby. The illustrated embodiments show six first connectors and three second connectors.

The above staple aperture design or connector assembly has many advantages for attaching gasket material or a graft material to a stent. Because the legs of the staple are folded around and imbedded within a pocket or the like, any risk of puncturing an inflation balloon is minimized. In addition, the structural integrity of the prosthesis is increased because staples more securely attach the graft material to the stent, as compared to prior art designs which use sutures or adhesives to attach the graft to the stent.

Staples 90 and 120 can be made from any number of materials known in the art, including tantalum alloys, platinum alloys or stainless steel, such as a grade of type 316 stainless steel. The staples may take on other configurations and shapes, and can be coated for lubricity purposes, wear resistance and for the prevention of corrosion. Essentially, the coating may be used for increased durability. The staples may be formed from a radiopaque material to identify the location of the staple, and to act as a marker to identify the location of a portion of the prosthesis. Using a different number of radiopaque staples on a distal end of a stent as compared to a proximal end further assists in identifying the position of the prosthesis.

Methods

A method in accordance with the present invention includes delivering and positioning a first prosthesis in a fluid conduit, such as an aorta. In preferred embodiments of the invention, the first prosthesis is a stent gasket, even more preferably, a stent gasket that expands automatically against the wall of the artery. As the stent gasket expands, proximal longitudinal legs allow the stent gasket diamond rings to expand, thereby anchoring the stent in place. The method also includes delivering and positioning at least one second prosthesis. In preferred embodiments of the invention, the second prosthesis is a bypass conduit for extending through an aneurysm. The second prosthesis is typically positioned within the first prosthesis, preferably into and through a hole in the first prosthesis cover. In most preferred embodiments of the invention, the hole is slightly smaller in diameter than the expanded diameter of the second prosthesis, thus sealingly engaging the second prosthesis in the first prosthesis. The sealed configuration of the second prosthesis within the first prosthesis forms a fluid pathway through the assembly or system, thereby bypassing the aneurysm.

A method according to the present invention further includes delivering a third prosthesis to the site of the aneurysm, and positioning the third prosthesis in mating engagement with the second prosthesis. In preferred embodiments of the invention, positioning the third prosthesis in mating engagement with the second prosthesis establishes a fluid flow path that bypasses the aneurysm.

Figure 7:
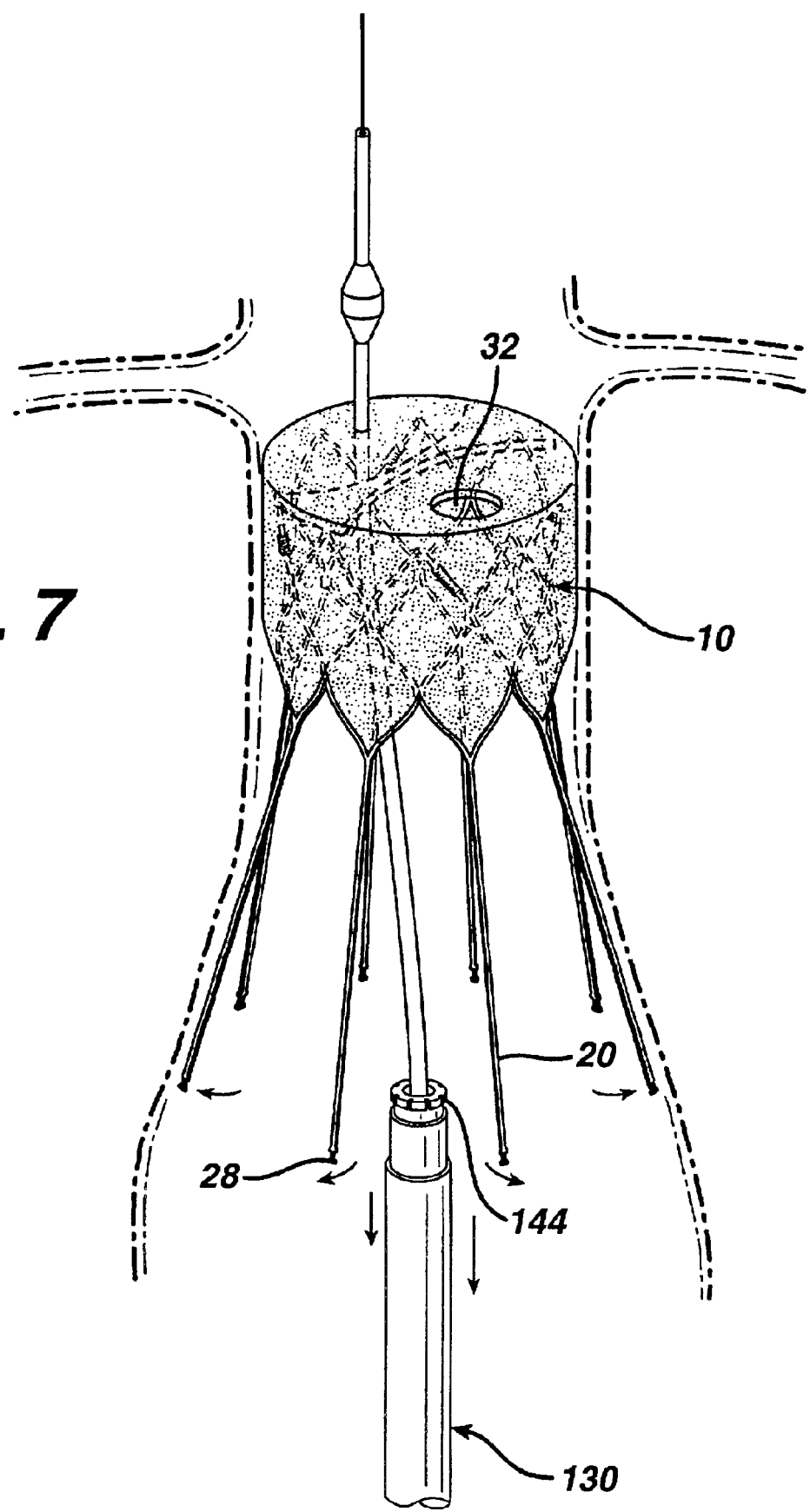
FIG. 7 is an elevation view of a fully deployed first prosthesis made in accordance with the present invention and an exemplary delivery system.

FIGS. 1, 7, and 15 generally show how the system of the present invention may be deployed in vivo. One skilled in the art will readily recognize that a typical delivery device 130, such as a catheter, includes a guidewire or the like that passes through an aperture in the cover 31 of the first prosthesis, and a collar or the like that releasably engages at least one anchor on the prosthesis. Once the anchors are released from the collar, the first prosthesis can expand, preferably automatically. The portion of the delivery device containing the collar can then be removed from the artery, typically leaving the guidewire in place, i.e., still positioned in an aperture of the first prosthesis cover. The guidewire may then be used to guide a second prosthesis into position within the first prosthesis.

In some exemplary embodiments of the present invention, the collar of the delivery device, engaged to the prosthesis, may be positioned within a sheath or the like until the prosthesis is delivered. In preferred embodiments of the invention, a portion of the prosthesis may be partially deployed and/or positioned. Once it is determined that the prosthesis is in its proper position, the collar may be pushed out of the sheath, thereby releasing the anchors from the collar. If the prosthesis is a self-expanding prosthesis, release of the flanges will allow the prosthesis to deploy automatically. If the prosthesis is not self-expanding, a deflated balloon or the like may be delivered to the interior of the prosthesis using the guidewire. When the balloon is inflated, it will expand the prosthesis into its fully deployed position, i.e., fully expanded radially.

A method according to the present invention includes providing a first prosthesis as described above, and delivering the first prosthesis to a site upstream of the aneurysm, and delivering and engaging a second prosthesis with the first prosthesis.

A method according to the present invention includes providing an extension or third prosthesis as described above, delivering the extension or third prosthesis to the site of the second prosthesis, aligning the extension or third prosthesis with the second prosthesis, and engaging the extension or third prosthesis with the second prosthesis.

In some exemplary embodiments of the invention, it may be desirable to align the respective prostheses by incorporating a distinctive pattern of markers or the like in each of the prostheses, and aligning a portion of the first pattern with a complementary portion on a second pattern.

As is evident to one skilled in the art, precisely placing a component(s) of the system may be critical. The physician must have precise placement of the components to ensure adequate repair of the aneurysm. The present invention allows the physician to nearly fully deploy a component within the body without fully releasing the entire component from the delivery device. The anchors releasably interlock with complementary structures, such as grooves, on the delivery device, and, if the physician decides that the placement of the component is incorrect, the outer member of the delivery device may be moved relative to an inner member, thereby resulting in the prosthesis being retrieved or retracted within the delivery device. The extended legs and anchors allow the physician to temporarily position the prosthesis before full deployment. Once the physician is satisfied with a prosthesis' position, the prosthesis may be released from its engagement with the delivery device.

In preferred embodiments of the invention, the system is used to bypass an abdominal aortic aneurysm (AAA). A method for treating or bypassing an AAA includes delivering, preferably percutaneously, a first prosthesis or precursor stent, or one of its components (e.g., the gasket member may be delivered separately, if desired). The components of the system are typically delivered through one or more of the common femoral arteries and deployed within the infrarenal neck, between an abdominal aortic aneurysm and the renal arteries of a patient. Once the first prosthesis is properly positioned or re-positioned, the legs and anchors are fully released from the delivery device. The delivery device for the precursor stent may then be removed, without removing the guidewire, and another guidewire may be inserted through the other femoral artery and into first prosthesis. If the second guidewire is on the wrong side of the interior of first prosthesis, it will contact the occlusive member and be prevented from easily advancing. The physician may then properly reposition the guidewire through hole 32.

Thereafter each delivery apparatus, each containing a sheathed second prosthesis, is inserted into common femoral arteries by sliding them over the guidewires; each of the two second prostheses are then positioned in the first prosthesis. Thereafter, the second prostheses may be either separately or simultaneously deployed.

After proper delivery, stent gasket 10 and prostheses 11*a* and 11*b* should appear as they do in FIG. 1. First prosthesis 10 along with its attached gasket material 30 is firmly secured within the infrarenal neck 101. The outward force of the second prostheses 11*a, b* on the stent gasket 10 help to secure the device within the body. The distal ends of the second prosthesis are firmly attached to the common iliac arteries 1 and 2. Thereafter blood will flow from the abdominal aorta through an exemplary system of the present invention comprising a first prosthesis and two second prostheses 11*a* and 11*b*, and into iliac arteries 1 and 2, thereby bypassing the aneurysmal sac 100.

One or more third prostheses may then be connected to the second prosthesis or prostheses. In some embodiments or the invention, the third prosthesis may be engaged to an upstream portion of the second prosthesis, or the third prosthesis may be engaged to a downstream portion of the second prosthesis, or combinations thereof.

It is important to note that even though self-expanding stents are utilized, balloons may be utilized for tacking them into position if necessary.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A system for bypassing an aneurysm comprising a bypass prosthesis for extending through a portion of an aneurysm said bypass prosthesis comprising an expandable stent having a graft material disposed on a surface of the stent and having a proximal end and distal end each, upon expansion, with lumen openings of a predetermined diameters; an extension prosthesis comprising an expandable stent having a graft material disposed on a surface of the stent, said stent defining a proximal, medial, and distal zones, said proximal zone having a first diameter upon expansion and said medial zone having a second diameter upon expansion where said first diameter is greater than said second diameter where the proximal zone flares from the medial zone, an open proximal lumen formed in a proximal zone and an open distal lumen formed in the distal zone, where predetermined diameter of said bypass prosthesis upon expansion corresponds to said first diameter of said extension prosthesis so that the proximal zone of the extension prosthesis matingly engages and is overlapped by the distal end of the bypass prosthesis to form fluid tight seal and where said extension prosthesis is configured to extend through another portion of said aneurysm; and a sealing prosthesis configured to receive said proximal end of said bypass prosthesis, said sealing prosthesis comprises a stent having a gasket material disposed on a surface of the stent, said stent defining a hollow tube having a distal open end and a covered proximal end, said proximal end of said sealing prosthesis being configured to engage the proximal end of the bypass prosthesis or a portion thereof.

2. The system of claim 1 wherein said proximal zone of the extension prosthesis flares for frictional, non-abrasive engagement with the bypass prosthesis.

3. The system of claim 2 wherein the flaring of said proximal zone of the extension prosthesis has a length corresponding to length of the overlap with the bypass prosthesis.

4. The system of claim 3 wherein the bypass prosthesis overlaps the proximal zone of the extension prosthesis by 30–50 mm.

5. The system of claim 4 wherein the bypass stent is focused inwardly to taper and the proximal zone of the stent of the extension prosthesis is focused outwardly and further comprising an open hoop.

6. The system of claim 2 further comprising at least one connector for engaging the bypass prosthesis with the extension prosthesis.

7. The system of claim 6 wherein said connector comprises a leg having a knobbed tip.

8. The system of claim 1 further comprising at least one anchor positioned in a distal portion the extension prosthesis.

9. The system of claim 1 further comprising at least one marker positioned in a distal portion of said bypass prosthesis, and at least one marker positioned in a proximal portion of said extension prosthesis.

10. The system of claim 9 wherein the distal portion of the bypass prosthesis comprises at least two markers, said markers forming a distinctive pattern.

11. The system of claim 9 wherein the proximal portion of the extension prosthesis comprises at least two markers, said markers forming a distinctive pattern.

* * * * *